United States Patent [19]

Baldwin et al.

[11] Patent Number: 5,698,566
[45] Date of Patent: Dec. 16, 1997

[54] NITROGEN-CONTAINING SPIROCYCLES

[75] Inventors: John J. Baldwin, Gwynedd Valley; David A. Claremon, Maple Glen; Jason M. Elliott, Blue Bell; Gerald S. Ponticello, Lansdale; David C. Remy, North Wales; Harold G. Selnick, Ambler, all of Pa.

[73] Assignee: Merck & Co., Inc., Rahway, N.J.

[21] Appl. No.: 505,179

[22] PCT Filed: Feb. 10, 1994

[86] PCT No.: PCT/US94/02097

§ 371 Date: Nov. 2, 1995

§ 102(e) Date: Nov. 2, 1995

[87] PCT Pub. No.: WO94/18204

PCT Pub. Date: Aug. 18, 1994

Related U.S. Application Data

[63] Continuation of Ser. No. 17,051, Feb. 12, 1993, abandoned.

[51] Int. Cl.$^6$ .................... A61K 31/44; C07D 221/00
[52] U.S. Cl. .................... 514/278; 546/16; 546/17
[58] Field of Search .................... 546/16, 17; 514/278

[56] References Cited

U.S. PATENT DOCUMENTS

| | | | |
|---|---|---|---|
| 5,206,240 | 4/1993 | Baldwin et al. | 514/231.5 |
| 5,382,587 | 1/1995 | Baldwin et al. | 514/278 |
| 5,439,914 | 8/1995 | Claremon et al. | 514/278 |
| 5,484,923 | 1/1996 | Cai et al. | 546/17 |

OTHER PUBLICATIONS

Elliott et al., "4–Oxospiro[benxopyran–2, 4'–piperidines] as Class III Antiarrhythmic Agents", Journal of Medicinal Chemistry, vol. 35, pp. 3973–3976, 1992.

*Primary Examiner*—Mukund J. Shah
*Assistant Examiner*—Brenda Coleman
*Attorney, Agent, or Firm*—Elliott Korsen; Francis P. Bigley; Mark R. Daniel

[57] ABSTRACT

A series of novel spirocycles of general structural formula:

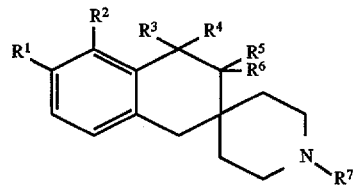

or a pharmaceutically acceptable salt, hydrate or crystal form thereof are presented, wherein $R^1 = H_3CSO_2NH—$, $H_3CO—$, alkylSO$_2$—, alkylCONH—, NO$_2$—;

$R^2 = H$, —OCH$_3$;

$R^3$ and $R^4$ taken together are =O, or $R^3$ is H and $R^4$ is OH;

$R^5 = R^6$ taken together are —CH$_2$—CH$_2$—, =CH$_2$;

$R^7$ is

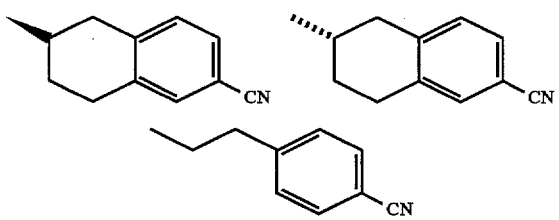

which are Class III antiarrhythmic agents and positive inotropic or cardiotonic agents.

11 Claims, No Drawings

NITROGEN-CONTAINING SPIROCYCLES

This application is a 371 of PCT/US 94/02097 filed on Feb. 10, 1994 which is a continuation of U.S. Ser. No. 08/017,051 filed on Feb. 12, 1993, now abandoned.

SUMMARY OF THE INVENTION

This invention is concerned with novel spirocycles of general structural formula:

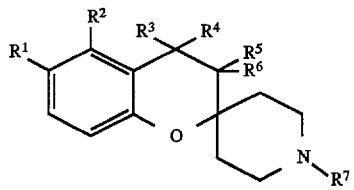

or a pharmaceutically acceptable salt, hydrate or crystal form thereof, wherein $R^1$=$H_3CSO_2NH$—, $H_3CO$—, alkyl$SO_2$—, alkylCONH—, $NO_2$—;

$R^2$=H, —$OCH_3$;

$R^3$ and $R^4$ taken together are =O, or $R^3$ is H and $R^4$ is OH;

$R^5$=$R^6$ taken together are —$CH_2$—$CH_2$—, =$CH_2$;

$R^7$ is

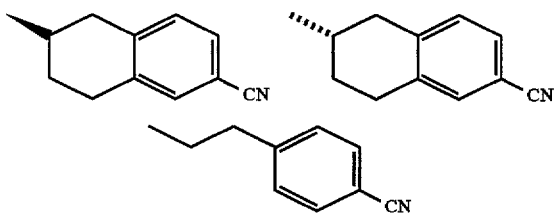

which are Class III antiarrhythmic agents and positive inotropic or cardiotonic agents, The invention is also concerned with pharmaceutical formulations comprising one or more of the novel compounds as active ingredient, either alone or in combination with one or more of a Class I, Class II or Class IV antiarrhythmic agent.

The invention is also concerned with a method of treatment of arrhythmia and impaired cardiac pump functions with the above-described novel compounds and formulations thereof.

The invention is further concerned with processes for preparing the novel compounds.

BACKGROUND OF THE INVENTION

Arrhythmias often occur as complications to cardiac diseases such as myocardial infarction and heart failure. In a serious case, arrhythmias give rise to a ventricular fibrillation and can cause sudden death.

Though various antiarrhythmic agents are now available on the market, those, having both satisfactory effects and high safety, have not been obtained. For example, antiarrythmic agents of Class I according to the classification of Vaughan-Williams which cause a selective inhibition of the maximum velocity of the upstroke of the action potential (Vmax) are inadequate for preventing ventricular fibrillation. In addition, they have problems regarding safety, namely, they cause a depression of the myocardial contractility and have a tendency to induce arrhythmias due to an inhibition of the impulse conduction. Beta-adrenoceptor blockers and calcium antagonists which belong to Class II and IV respectively, have a defect that their effects are either limited to a certain type of arrhythmia or are contraindicated because of their cardiac depressant properties in certain patients with cardiovascular disease. Their safety, however, is higher than that of the antiarrhythmic agents of Class I.

Antiarrythmic agents of Class III are drugs which cause a selective prolongation of the duration of the action potential without a significant depression of the Vmax. Drugs in this class are limited. Examples such as sotalol and amiodarone have been shown to possess Class III properties. Sotalol also possesses Class II effects which may cause cardiac depression and be contraindicated in certain susceptible patients. Also, amiodarone is severely limited by side effects. Drugs of this class are expected to be effective in preventing ventricular fibrillations. Pure Class III agents, by definition, are not considered to cause myocardial depression or an induction of arrhythmias due to the inhibition of the action potential conduction as seen with Class I antiarrhythmic agents.

A number of antiarrhythmic agents have been reported in the literature, such as those disclosed in:

(1) EP 397,121-A,
(2) EP 300,908-A,
(3) EP 307,121,
(4) U.S. Pat. No. 4,629,739,
(5) U.S. Pat. No. 4,544,654,
(6) U.S. Pat. No. 4,788,196,
(7) EP application 88302597.5,
(8) EP application 88302598.3,
(9) EP application 88302270.9,
(10) EP application 88302600.7,
(11) EP application 88302599.1,
(12) EP application 88300962.3,
(13) EP application 235,752,
(14) DE 3633977-A1,
(15) U.S. Pat. No. 4,804,662,
(16) U.S. Pat. No. 4,797,401,
(17) U.S. Pat. No. 4,806,555,
(18) U.S. Pat. No. 4,806,536.

Compounds of similar structure are found in Japanese patent publication 88-63533-B of Daiichi Pharmaceutical Co.; J. Med. Chem., 19, 1315 (1976) by Bauer et al; Iorio et al in Il. Farmaco-Ed Sci., 32, 212–219 (1977): Houlihan et al, U.S. Pat. No. 3,686,186; Davis et al, U.S. Pat. No. 4,420,485; Kealey, U.S. Pat. No. 4,810,792; Parham et al, J. Org. Chem., 41, 2629 (1976). None of the compounds disclosed in the foregoing references are alleged to have antiarrhythmic activity.

Now with the present invention, there is provided as antiarrhythmic agent new compounds with an increased degree of activity.

DETAILED DESCRIPTION OF THE INVENTION

The novel compound of this invention has structural formula:

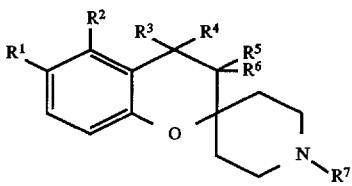

or a pharmaceutically acceptable salt, hydrate or crystal form thereof;
wherein:

$R^1 = H_3CSO_2NH-$, $H_3CO-$, $alkylSO_2-$, $alkylCONH-$, $NO_2-$;

$R^2 = H$, $-OCH_3$;

$R^3$ and $R^4$ taken together are $=O$ or $R^3 = H$ and $R^4 = OH$;

$R^5$ and $R^6 =$ taken together are $-CH_2-CH_2-$, $=CH_2$;

$R^7$ is

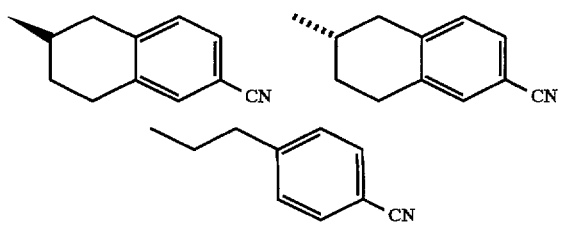

In a preferred embodiment of the novel compound,
$R^1 = CH_3SO_2NH-$;
$R^2 = H$;
$R^3$ and $R^4$ together are $=O$ or $R^3 = H$ and $R^4 = OH$;
$R^5$ and $R^6$ taken together as $=CH_2$, $-CH_2-CH_2-$,
$R^7$ is

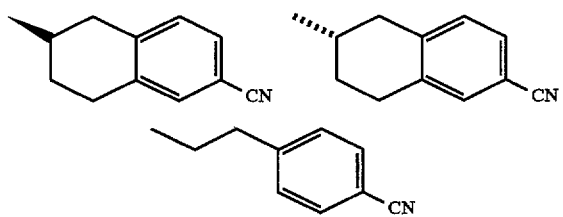

In particular it is preferred that
$R^1 = CH_3SO_2NH-$
$R^2 = -H$;
$R^3$ and $R^4$ together are $=O$;
$R^5$ and $R^6$ together are $-CH_2-CH_2-$, $=CH_2$; $R^7$ is

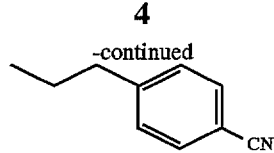

It is also preferred that
$R^1 = CH_3SO_2NH-$
$R^2 = -H$:
$R^3$ and $R^4$ taken together are $=O$;
$R^5$ and $R^6$ taken together are $=CH_2$;
$R^7$ is

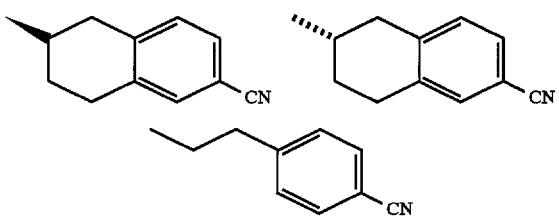

It is also preferred that
$R^1 = CH_3SO_2NH-$
$R^2 = -H$;
$R^3 = -H$;
$R^4 = -OH$;
$R^5$ and $R^6$ taken together are $-CH_2-CH_2-$;
$R^7$ is

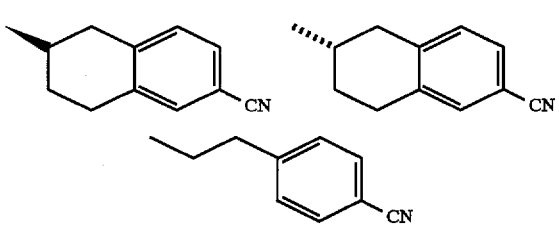

It is even more preferred that
$R^1 = CH_3SO_2NH-$
$R^2 = -H$;
$R^3 = H$;
$R^4 = OH$;
$R^5$ and $R^6$ taken together are $=CH_2$;
$R^7$ is

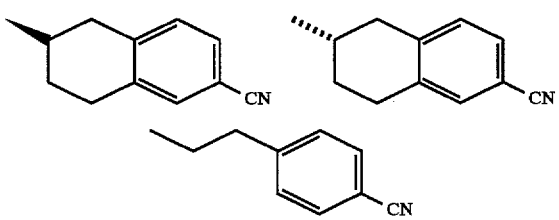

or the hydrochloride, maleate, methanesulfonate, tri-citrate or isethionate salt of this base.

Preferred compounds include:

1'-[2-(4-Cyanophenyl)ethyl]-3,4-dihydro-6-methanesulfonamido-3-methylenespiro(2H-1-benzopyran-2,4'-piperidine)-4-one 1"-[2-(4-Cyanophenyl)ethyl]-6'-methanesulfonamidodispiro[cyclopropane-1,3'(4'H)-[2H-1]benzopyran-2',4"-piperidine]-4'-one 1"-[2-(4-Cyanophenyl)ethyl)-6'-methanesulfonamidodispiro[cyclopropane-1,3'(4'H)-[2H-1]benzopyran-2',4"-piperidine[-4'-one hydrochloride 1"-[2-(4-Cyanophenyl)ethyl]-6'-methanesulfonamidodispiro[cyclopropane-1,3'(4'H)-[2H-1]-benzopyran-2',4"-piperidine]-4'-one maleate 1"-[2-(4-Cyanophenyl)ethyl]-6'-methanesulfonamidodispiro[cyclopropane-1,3'(4'H)-[2H-1]benzopyran-2',4"-piperidine]-4'-one methanesulfonate Tetra{1"-[2-(4-cyanophenyl)ethyl]-6'-methanesulfonamidodispiro[cyclopropane-1,3'(4'H)-[2H-1]benzopyran-2',4"-piperidine]-4'-one}tricitrate 1"-[2-(4-Cyanophenyl)ethyl]-6'-methanesulfonamidodispiro[cyclopropane-1,3'(4'H)-[2H-1]benzopyran- 2',4"-piperidine]-4'-one isethionate (4'RS)-1"-[2-(4-Cyanophenyl)ethyl]-6'-methanesulfonamidodispiro[cyclopropane-1,3'(4'H)-[2H-1]benzopyran-2',4"-piperidine]-4'-ol

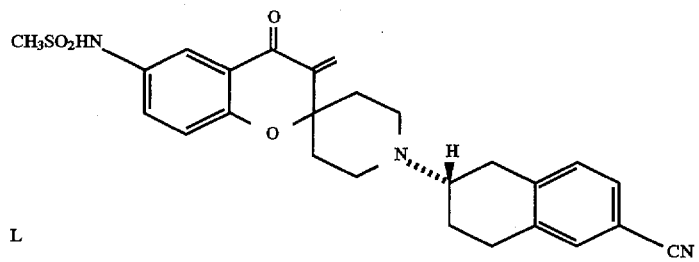

(−)-(2″S)-1′-[(6-Cyano-1,2,3,4-tetrahydronaphthalene)-2-yl]1-3,4-dihydro-6-methanesulfonamido-3-methylenespiro(2H-1-benzopyran-2,4′-piperidine)-4-one

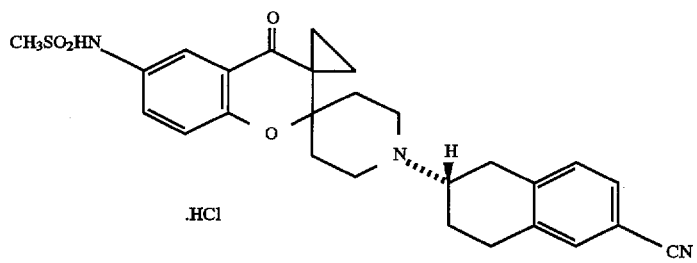

(−)-(2‴S)-1″-[-(6-Cyano-1,2,3,4-tetrahydronaphthalene)-2-yl]-6′-methanesulfonamidodispiro[cyclopropane-1,3′(4′H)-[2H-1]benzopyran-2′,4″-piperidine]-4′-one hydrochloride

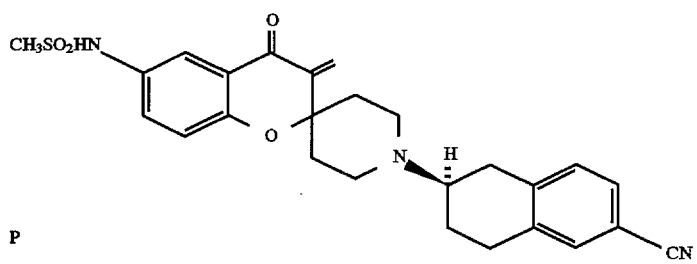

P (+)-(2″R)-1′-[(6-Cyano-1,2,3,4-tetrahydronaphthalene)-2-yl]-3,4-dihydro-6-methanesulfonamido-3-methylenespiro(2H-1-benzopyran-2,4′-piperidine)-4-one

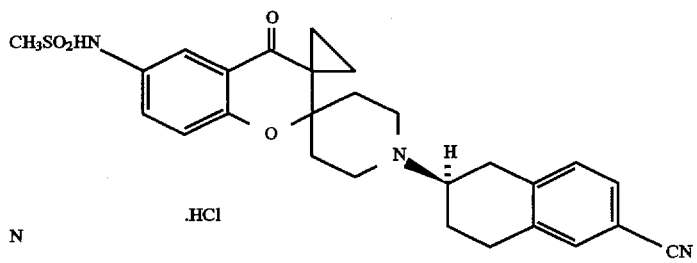

N (+)-(2‴R)-1-[(6-Cyano-1,2,3,4-tetrahydronaphthalene)-2-yl]-6′-methanesulfonamidodispiro[cyclopropane-1,3′

(4'H)-[2H-1]benzopyran-2',4''-piperidine]-4'-one hydrochloride

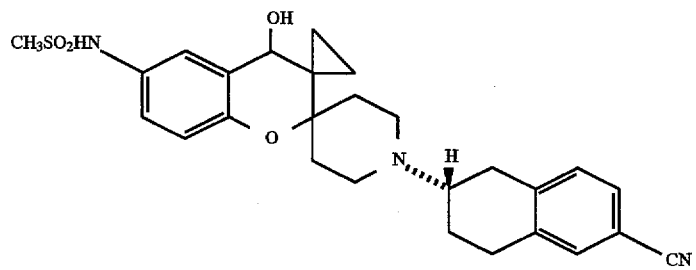

(−)-(4'RS,2'''S)-1''-[(6-Cyano-1,2,3,4-tetrahydronaphthalene)-2-yl]-6'-methanesulfonamidodispiro[cyclopropane-1,3'(4'H)-[2H-1]benzopyran-2',4''-piperidine]-4'-ol; or

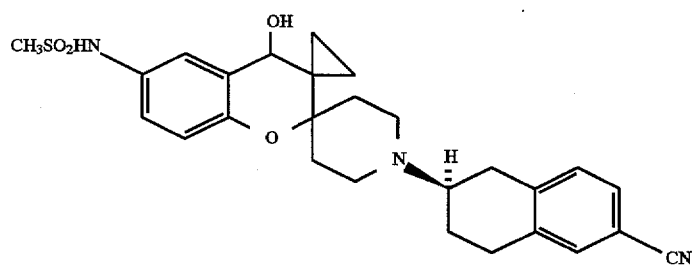

(+)-(4'RS,2'''R)-1''-[(6-Cyano-1,2,3,4-tetrahydronaphthalene)-2-yl]-6'-methanesulfonamidodispiro[cyclopropane-1,3'(4'H)-[2H-1]benzopyran-2',4''-piperidine]-4'-ol and pharmaceutically acceptable salts, hydrates and crystal forms thereof.

The term "alkyl", if the number of carbons is unspecified, means $C_{1-6}$alkyl and "alkyl" of three or more carbon atoms includes straight chain, branched chain and cycloalkyl.

Also included within the scope of the present invention are the non-toxic pharmaceutically acceptable salts of the novel compounds. Acid addition salts are formed by mixing a solution of the compound with a solution of a pharmaceutically acceptable non-toxic acid such as hydrochloric acid, fumaric acid, maleic acid, methanesulfonic acid, isethionic acid, succinic acid, acetic acid, citric acid, tartaric acid, phosphoric acid, or the like. Also included within the scope of this invention are N-oxides. Furthermore, included within the scope of this invention are $C_{1-6}$alkyl, $C_{1-6}$alkyl-phenyl, and $C_{3-6}$alkenyl-phenyl quaternary ammonium salts.

Also included within the scope of this invention are diastereomers and enantiomers of the novel compounds and mixtures thereof. In particular Inventors: please pick one of the compounds from those claimed that contains a chiral center and enter it here as an example and then complete the following sentence chirality is introduced and the racemate and both enantiomers thereof are embraced within the scope of this invention.

The novel processes of this invention can be exemplified by the following Reaction Schemes:

SCHEME I

Preparation of (+/−)-1,4-dioxa-8-(6'-bromo-1',2',3',4'-tetrahydronaphth-2'-yl)-8-azaspiro[4,5]decane and associated phenyl cyanate

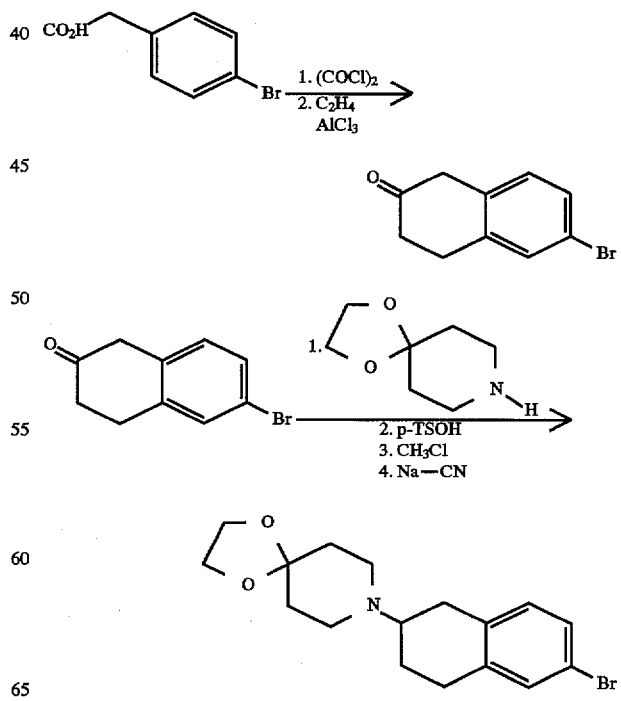

The mixture was cooled, and concentrated to an oil in vacuo. The oil was dissolved in anhydrous tetrahydrofuran (1.5 L) and cooled to 0° C. under argon. Dry HCl gas was introduced (at below 5° C.) and a solid precipitate formed. Sodium cyanoborohydride (36.3 g, 578 mmol) was added in four portions. The reaction was allowed to warm gradually to room temperature and stirred 16 hours. This was quenched with 1N aqueous sodium hydroxide (500 mL) and stirred for 0.5 hours (pH=13.5). The mixture was concentrated on a rotary evaporator to remove THF, and diluted with 1N NaOH (1.1 L) and diethyl ether (1.5 L). This mixture was stirred 15 minutes and the layers were separated and the aqueous layer was washed with diethyl ether (2×200 mL). The organic layers were combined, washed with water (2×500 mL) and saturated aqueous NaCl (2×250 mL) and then with 1N HCl (1×1.0 L, 2×500 mL). The acid extracts were combined, stirred with methylene chloride (1.0 L), and basified with 40% aqueous NaOH (pH=10). The layers were separated, and the aqueous layer extracted with methylene chloride (500 mL). The methylene chloride extracts were combined, dried $Na_2SO_4$), and concentrated to an oil. The oil was flushed with toluene (2×400 mL) and dried in vacuo to give the title compound as a solid on standing (128.8 g. 87%) which was greater then 98% pure by HPLC and used in the next step without purification. Note: The amount of excess HCl gas present (pH=3–4, THF suspension on wet pH paper) critically determines the yield free amine. Additional HCl may be added during the introduction of the cyano borohydride. In runs in which the pH was not adjusted properly the yield was reduced to 50%; the balance being a borane complex which was isolated from the either layer. This borane complex could be quantitatively convened to the free amino by heating in 40% aqueous NaOH/ethylene glycol (1:1) at 100° C.

Preparation of Phenyl cyanate is accomplished by a modification of the procedure described in Organic Syntheses, 61, 35 (1983). A 3-necked, 2 L round bottom lask, equipped with a 500 mL pressure equalized dropping funnel, a mechanical stirrer and a thermometer, was charged with water and cooled in an ice-salt bath. Cyanogen bromide (189.1 g, 1.78 mol) was added and the mixture was stirred for 5 minutes. Phenol (160.0 g, 1.7 mol) in carbon tetrachloride (535 mL) was added in one portion. The mixture was stirred vigorously while triethylamine (236.9 mL, 172.0 g, 1.7 mol) was added dropwise at a rate such that the reaction temperature did not exceed 5° C. (total addition time=45 minutes.). The mixture was stirred for a further 15 minutes then transferred to a 2 L separatory funnel. The organic layer was separated and the aqueous layer was extracted with carbon tetrachloride (2×90 mL). The combined organic layers were washed with water (3×90 mL) then dried by stirring with phosphorus pentoxide (10 g) for 15 minutes. The mixture was filtered and the solvent was evaporated under reduced pressure (water aspirator) at 20° C. to give a yellow oil. Polyphosphate exster (Y. Kanaoka, et al., Chem. Pharm. Bull, 13, 1065–1072 (1965)) (0.2 ml) was added and the mixture was distilled under reduced pressure through a 15 cm vigrex column to give phenyl cyanate (165.8 g. 82%) as a colorless oil, having a boiling point of 79°–82° C. (16 mm Hg). The product was stored under nitrogen at –10° C. (freezes).

Preparation of (±)-1,4-dioxa-8-(6'-cyano-1',2',3',4'-tetrahydronaphth-2'-yl)-8-azaspiro[4,5]decane as follows. (±)-1,4 dioxa-8-(6'-bromo-1',2',3',4'-tetrahydronaphth -2'-yl) -8-azaspiro[4,5]decane (70.4 g, 0.2 mol) under nitrogen in a 1 L round bottom flask was dissolved in anhydrous THF (600 mL, distilled from Na/benzophenone) and cooled to –75° C. Phenyl cyanate (26.06 ml, 28.5 g, 0.24 mol) dissolved in anhydrous THF (400 mL) under nitrogen in a 2 L round bottom flask equipped with a digital thermometer was cooled to –75° C. n-Butyl lithium (1.6M in hexane, 137.5 mL. 0.22 mmol) was added over 5 minutes to the bromide solution. Further n-butyl lithium (12.5 mL, 0.02 mmol) was added to phenyl cyanate solution. After 5 minutes, the lithiated bromide solution was added over 5 minutes, via cannula, to the phenyl cyanate solution (reaction temperature rises to –35° C.). The mixture was stirred and cooled to –75° C. for 30 minutes then the cooling bath was removed and HCl-water (1M, 200 mL) was added with vigorous stirring. The mixture was warmed to room temperature, diluted with HCl-water (1M, 1800 mL) and washed with ether (2×1000 mL). Methylene chloride (1000 mL) was added and the mixture was stirred and cooled in ice during the addition of aqueous sodium hydroxide (10M, 180 mL). The layers were separated, and the aqueous layer was extracted with methylene chloride (500 mL). The combined organic layers were dried ($Na_2SO_4$), and the solvent was evaporated under reduced pressure to give crude (±) 1,4-dioxa-8-(6'-cyano-1',2',3',4'-tetrahydronaphth-2'yl)-8-azaspiro-[4,5]-decane as a tan solid (56.2 g). Crude (±) 1,4-dioxa-8-(6'-cyano-1',2',3',4'-tetrahydronaphth-2'yl)-8-azaspiro-[4,5]-decane in three batches (56.4 g, 56.2 g, 27.7 g; total 140.3 g) were separately dissolved in refluxing methyl-cyclohexane (1000 mL each) and combined by decanting into a 5 L, 4-necked flask equipped with a mechanical stirrer, thermometer, reflux condenser and a stopper. The mixture was heated to reflux (clear solution formed), then allowed to cool with stirring to room temperature, then to 5° C. The mixture was stored at –15° C. for 15 hours. The solid was collected by filtration, washed with cold methylcyclohexane (2×150 mL) and dried in vacuo at room temperature to give the spirodecane as a pale yellow solid (121.3 g). having a melting point of 136°–138° C. Purity was determined to be 99.3%.

Resolution of 1,4-dioxa-8-(6'-cyano-1',2',3',4'-tetrahydronaphth-2'yl)-8-azaspiro-[4,5]-decane.

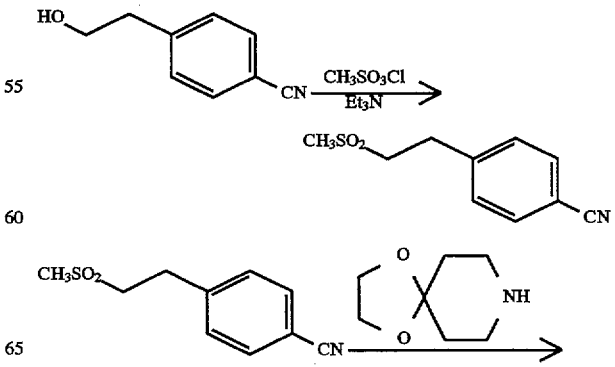

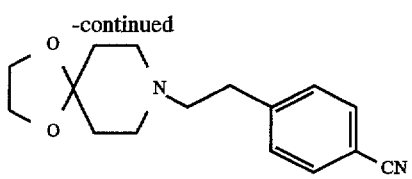

The process of scheme 3 is shown as follows:

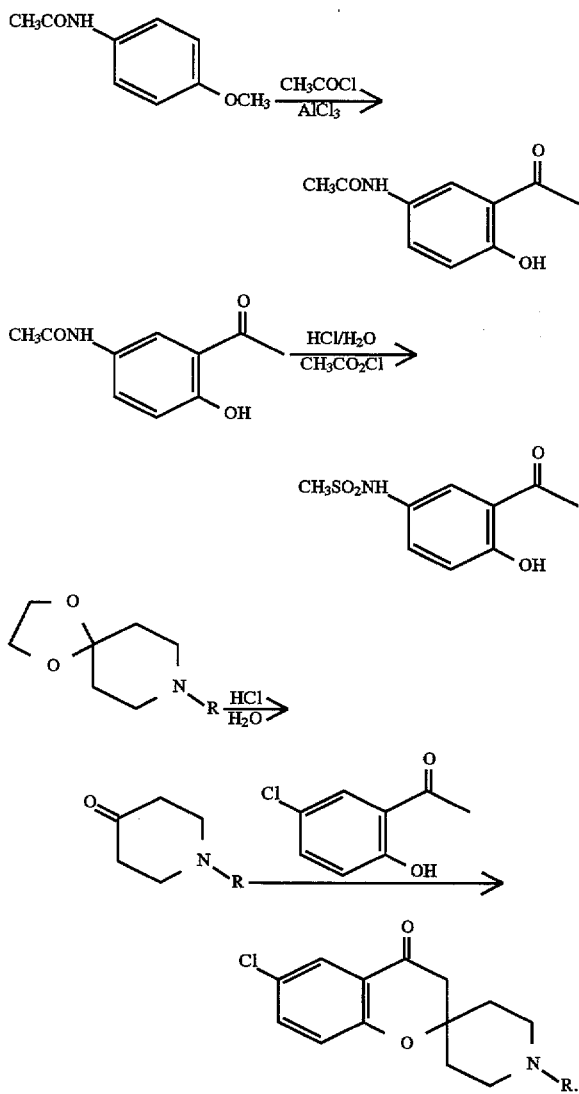

The process of Scheme I comprises the novel compounds of the present invention, have the pharmacological properties required for the antiarrhythmic agents of Class III, namely the prolongation of the myocardial action potential in vitro, without a significant depression of the Vmax, and the prolongation of QTc-interval in anesthetized dogs.

In addition these compounds also have the pharmacological properties required for the antiarrhythmic agents of Class III. Moreover, the members of both groups of compounds in general are much more potent than the reference drug, sotalol.

These compounds are effective in treating and preventing all types of arrhythmias including ventricular and atrial (supraventricular) arrhythmias. The compounds of the present invention are especially useful to control reentrant arrhythmias and prevent sudden death due to the ventricular fibrillation. These compounds are also effective in treating and preventing impaired cardiac pump functions.

In the novel method of this invention of treating arrhythmia, one of the compounds or pharmaceutically acceptable salt thereof, is administered in an amount ranging from about 0.0001 to about 20 mg per kg of body weight per day, preferably from about 0.001 to about 10 mg per kg of body weight per day in a single dose or in 2 to 4 divided doses.

These compounds can be administered as the sole active ingredient or in combination with other antiarrhythmic agents or other cardiovascular agents.

These compounds, or pharmaceutically acceptable salts thereof, in the described dosages, are administered orally, intraperitoneally, subcutaneously, intramuscularly, transdermally, sublingually or intravenously. They are preferably administered intravenously or orally, for example in the form of tablets, troches, capsules, elixirs, suspensions, syrups, wafers, chewing gum, or the like prepared by an recognized procedures. The amount of active compound in such therapeutically useful compositions or preparations is such that a suitable dosage will be obtained.

The following examples are given for the purpose of illustrating the present invention and shall not be construed as being limitations on the scope or spirit of the instant invention.

EXAMPLE 1

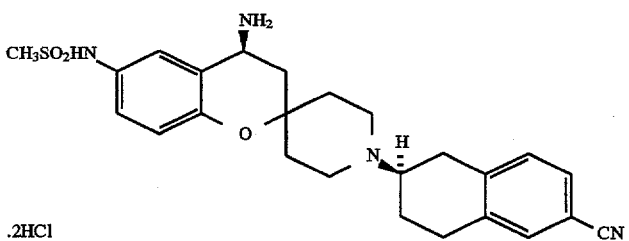

(4S,2"R)-1'-[(6-Cyano-1,2,3,4-tetrahydronaphthalene)-2-yl]-3,4-dihydro-6-methanesulfonamidospiro(2H-1-benzopyran-2,4'-piperidine)-4-amine dihydrochloride (+)-(4R, 2"R)-1'-[(6-Cyano-1,2,3,4-tetrahydronaphthalene)-2-yl]-3,4-dihydro-6-methanesulfonamidospiro(2H-1-benzopyran-2,4'-piperidine)-4-ol (3.60 g. 7.7 mmol) was dissolved in methylene chloride (120 ml) and cooled to −50° C. A solution of methanesulfonic anhydride (3.22 g. 18.5 mmol) in methylene chloride (35 ml) was added and the mixture was stirred at −45° C. A solution of diisopropylethylamine (2.75 ml. 2.04 g. 15.8 mmol) in methylene chloride (10 ml) was added slowly and the mixture was stirred at −20° C. for 15 min. A solution of tetrabutylammonium azide (8.32 g, 29.1 mmol) in methylene chloride (10 ml) was added slowly and the mixture was stirred at room temperature for 1 h. The mixture was filtered through silica gel washing with methylene chloride (500 ml) then with ethyl acetate (3000 ml). The ethyl acetate fractions were evaporated under reduced pressure to give a colorless foam (4.07 g). The residue was dissolved in methanol (200 ml), aqueous sodium hydroxide (1M, 100 ml) and methylene chloride (50 ml) were added and the mixture was stirred at room temperature for 3 h. The methanol was evaporated under reduced pressure, water (100 ml) and methlene chloride (250 ml) were added and the pH was adjusted to 9.0 with hydrochloric acid (conc.) The layers were separated and the aqueous layer was extracted with methylene chloride (125 ml). The combined organic fractions were dried ($Na_2SO_4$) and evaporated under reduced pressure to give a colorless foam (3.70 g). The residue was dissolved in ethanol (300 ml), palladium on carbon (10%, 0.75 g) was added and the mixture was stirred under hydrogen (1 Atm.) for 16 h. The mixture was filtered through celite and the solvent was evaporated under reduced pressure to give a colorless foam (3.44 g). A sample (0.5 g) was purified by flash column chromatography on silica gel, eluting with $CH_2Cl_2$/MeOH/$NH_3$ (Aq.) (95:5:1) to give (4S,2"R)-1'-[(6-cyano-1,2,3,4-tetrahydronaphthalene)-2-yl]-3,4-dihydro-6-methanesulfonamidospiro(2H-1-benzopyran-2,4'-piperidine)-4-amine (0.38 g. 73%). The residue was dissolved in ethyl acetate (20 ml) and HCl-$^i$PrOH (1.3M, 1.6 ml) was added dropwise with stirring. The mixture was stirred at ambient temperature for 1 h., hexane (50 ml) was added slowly and the mixture was stirred at ambient temperature for 1 h. The solid was collected and dried in vacuo at room temperature to give the dihydrochloride as a colorless solid (0.403 g).

m.p. 242°–245° C. (dec.).

Elementary analysis for $C_{25}H_{30}N_4O_3S.2HCl.H_2O$: Calculated; C 53.85; H 6.15; N 10.05%. Found; C 53.88; H 6.23; N 10.08%.

EXAMPLE 2

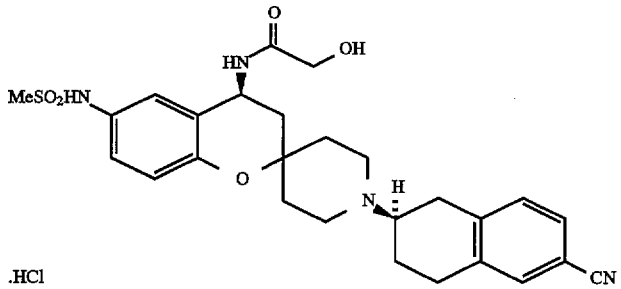

.HCl

(−)-(4S,2"R)-1'-(6-Cyano-1,2,3,4-tetrahydronaphthalene)-2-yl]-3,4-dihydro-4-(2-hydroxyacetamido)-6-methanesulfonamidospiro(2H-1-benzopyran-2,4'-piperidine)hydrochloride 1-(3-Dimethylaminopropyl)-3-ethylcarbodiimide hydrochloride (57 mg, 0.30 mmol) was added to a stirred, cooled (0° C.) solution of (4S,2"R)-1'-[(6-cyano-1,2,3,4-tetrahydronaphthalene)-2-yl]-3,4-dihydro-6-methanesulfonamidospiro(2H-1-benzopyran-2,4'-piperidine)-4-amine 125 mg, 0.27 mmol), glycolic acid (22 mg, 0.30 mmol) and 1-hydroxybenzotriazole (47 mg, 0.30 mmol) in DMF (4 ml). The mixture was stirred at room temperature for 18 h., poured into saturated aqueous sodium hydrogen carbonate (30 ml) and extracted with ethyl acetate (4×25 ml). The combined organic fractions were washed with saturated aqueous sodium hydrogen carbonate (3×10 ml), dried ($MgSO_4$) and evaporated under reduced pressure. The residue was purified by flash column chromatography on silica gel, eluting with $CH_2Cl_2$/MeOH/$NH_3$ (Aq.) (95:5:0.5 increasing to 92:8:0.8) to give a colorless solid (92 mg, 65%). The residue was suspended in ethanol (1 ml) and HCl-EtOH (6M, 0.5 ml) was added dropwise with stirring. The mixture was stirred at ambient temperature for 30 min. and the solvent was evaporated under reduced pressure. The solid was triturated with EtOH/$Et_2O$ (1:1) then refrigerated over night. The solid was collected and dried in vacuo at 60° C. to give the hydrochloride as a colorless solid (74 mg), m.p. 326° C., $[\alpha]_d$ −16.0° (c=0.062, $H_2O$).

Elementary analysis for $C_{27}H_{32}N_4O_5S.HCl.1.05H_2O$: Calculated; C 55.91; H 6.10; N 9.66%. Found; C 55.80; H 5.70; N 9.38%.

EXAMPLE 3

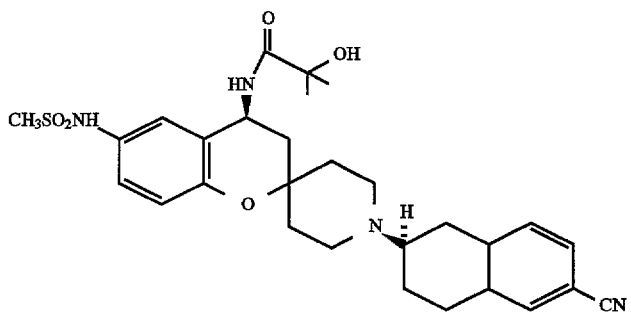

(−)-(4S,2"R)-1'-[(6-Cyano-1,2,3,4-tetrahydronaphthalene)-2-yl]-3,4-dihydro-4-[(2-hydroxy-2-methyl)propanamido]-6-methanesulfonamidospiro(2H-1-benzopyran-2,4'-piperidine)hydrochloride 1-(3-Dimethylaminopropyl)-3-ethylcarbodiimide hydrochloride (57 mg, 0.30 mmol) was added to a stirred, cooled (0° C.) solution of (4S,2"R)-1'-[(6-cyano-1,2,3,4-tetrahydronaphthalene)-2-yl]-3,4-dihydro-6-methanesulfonamidospiro(2H-1-benzopyran-2,4'-piperidine)-4-amine (125 mg, 0.27 mmol), 2-hydroxyisobutyric acid (22 mg, 0.30 mmol) and 1-hydroxybenzotriazole (31 mg. 0.30 mmol) in DMF (4 ml). The mixture was stirred at room temperature for 18 h., poured into saturated aqueous sodium hydrogen carbonate (30 ml) and extracted with ethyl acetate (4×20 ml). The combined organic fractions were washed with brine, dried (MgSO$_4$) and evaporated under reduced pressure. The residue was purified by flash column chromatography on silica gel, eluting with CH$_2$Cl$_2$/MeOH/NH$_3$ (Aq.) (95:5:0.5) to give a colorless foam (106 mg, 71%). The residue was suspended in ethanol (1 ml) and HCl-EtOH (6M, 1 ml) was added dropwise with stirring. The mixture was stirred at ambient temperature for 10 min. and the solvent was evaporated under reduced pressure. The solid was triturated with ether then refrigerated for 45 min. The solid was collected and dried in vacuo at 60° C. to give the hydrochloride as a colorless solid (88 mg), m.p. 297° C., [α]$_d$ −20.0° (c=0.045, H$_2$O).

Elementary analysis for C$_{29}$H$_{36}$N$_4$O$_5$S.HCl.1.85H$_2$O: Calculated; C 56.04; H 6.44; N 9.02%. Found; C 56.08; H 6.14; N 8.72%.

EXAMPLE 4

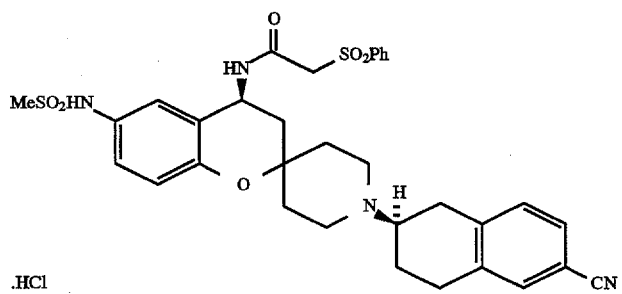

(−)-(4S,2"R)-1'[(6-Cyano-1,2,3,4-tetrahydronaphthalene)-2-yl]-3,4-dihydro-6-methanesulfonamido-4-[2-(phenylsulfonyl)acetamido]spiro(2H-1-benzopyran-2,4'-piperidine) hydrochloride 1-(3-Dimethylaminopropyl)-3-ethylcarbodiimide hydrochloride (86 mg, 0.44 mmol) was added to a stirred, cooled (0° C.) solution of (4S,2"R)-1'-(6-cyano-1,2,3,4-tetrahydronaphthalene)-2-yl]-3,4-dihydro-6-methanesulfonamidospiro(2H-1-benzopyran-2,4'-piperidine)-4-amine (186 mg, 0.40 mmol), phenylsulfonylacetic acid (8;8 mg, 0.44 mmol), 1-hydroxybenzotriazole (67 mg, 0.44 mmol) and DMF (4 drops) in methylene chloride (2 ml). The mixture was stirred at room temperature for 18 h., poured into saturated aqueous sodium hydrogen carbonate (30 ml) and extracted with methylene chloride (4×50 ml). The combined organic fractions were dried (Na$_2$SO$_4$) and evaporated under reduced pressure. The residue was purified by flash column chromatography on silica gel, eluting with CH$_2$Cl$_2$/MeOH/NH$_3$ (Aq.) (98:2:0.2 increasing to 94:6:0.6) to give a colorless solid (86 mg, 32%). The residue was suspended in ethanol (10 ml) and HCl-EtOH (6M, 2 ml) was added dropwise with stirring. The mixture was stirred at ambient temperature for 30 min. and the solvent was evaporated under reduced pressure. The solid was triturated with ether, collected and dried in vacuo at 80° C. to give the hydrochloride as a colorless solid (72 mg), m.p.>290° C., [α]$_d$ −3.9° (c=0.128, NaOH-H$_2$O/MeOH).

Elementary analysis for C$_{33}$H$_{36}$N$_4$O$_6$S$_2$.HCl.1.15H$_2$O: Calculated; C 56.14; H 5.61; N 7.94%. Found; C 56.13; H 5.38; N 8.04%.

EXAMPLE 5

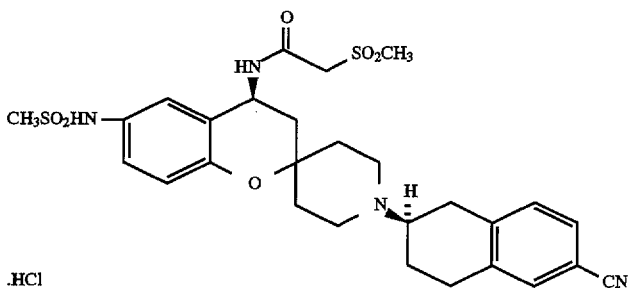

(−)-(4S,2"R)-1'-[(6-Cyano-1,2,3,4-tetrahydronaphthalene)-2-yl]-3,4-dihydro-6-methanesulfonamido-4-[2-(methanesulfonyl)acetamido]spiro -(2H-1-benzopyran-2,4'-piperidine) hydrochloride 1-(3-Dimethylaminopropyl)-3-ethylcarbodiimide hydrochloride (84 mg, 0.44 mmol) was added to a stirred, cooled (0° C.) solution of (4S,2"R)-1'-[(6-cyano-1,2,3,4-tetrahydronaphthalene)-2-yl]-3,4-dihydro-6-methanesulfonamidospiro(2H-1-benzopyran-2,4'-piperidine)-4-amine (186 mg, 0.40 mmol), methanesulfonylacetic acid (61 mg, 0.44 mmol), 1-hydroxybenzotriazole (67 mg, 0.44 mmol) and DMF (4 drops) in methylene chloride (2 ml). The mixture was stirred at room temperature for 18 h., poured into saturated aqueous sodium hydrogen carbonate (30 ml) and extracted with methylene chloride (4×20 ml). The combined organic fractions were washed with brine (20 ml) dried (Na$_2$SO$_4$) and evaporated under reduced pressure. The residue was purified by flash column chromatography on silica gel, eluting with CH$_2$Cl$_2$/MeOH/NH$_3$ (Aq.) (98:2:0.2 increasing to 92:8:0.8) to give a colorless foam (178 mg, 76%). The residue was suspended in ethanol (3 ml) and HCl-EtOH (6M, 1 ml) was added dropwise with stirring. The mixture was refrigerated over night and the solid was collected and dried in vacuo at 80° C. to give the hydrochloride as a colorless solid (164 mg), m.p.>260° C., [α]$_d$ −10.0° (c=0.08, HCl-H$_2$O).

Elementary analysis for C$_{28}$H$_{34}$N$_4$O$_6$S$_2$.HCl: Calculated; C 53.96; H 5.66; N 8.99%. Found; C 53.89; H 5.60; N 8.78%.

EXAMPLE 6

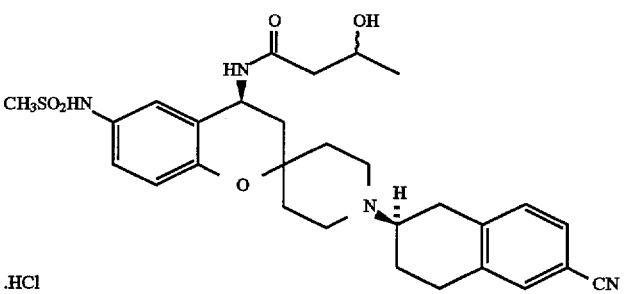

(−)-(3RS,4S,2"R)-1'-[(6-Cyano-1,2,3,4-tetrahydronaphthalene)-2-yl]-3,4-dihydro-4-(3-hydroxybutanamido)-6-methanesulfonamidospiro (2H-1-benzopyran-2,4'-piperidine)hydrochloride 1-(3-Dimethylaminopropyl)-3-ethylcarbodiimide hydrochloride (57 mg, 0.30 mmol) was added to a stirred, cooled (0° C.) solution of (4S,2"R)-1'-[(6-cyano-1,2,3,4-tetrahydronaphthalene)-2-yl]3,4-dihydro-6-methanesulfonamidospiro(2H-1-benzopyran-2,4'-piperidine)-4-amine (125 mg, 0.27 mmol), (3RS)-3-hydroxybutyric acid (30 mg, 0.30 mmol) and 1-hydroxybenzotriazole (46 mg, 0.30 mmol) in methylene chloride (1 ml). The mixture was stirred at room temperature for 18 h., poured into saturated aqueous sodium hydrogen carbonate (20 ml) and the layers were separated. The aqueous layer was extracted with ethyl acetate (3×50 ml) and the combined organic fractions were dried (MgSO$_4$) and evaporated under reduced pressure. The residue was purified by flash column chromatography on silica gel, eluting with CH$_2$Cl$_2$/MeOH/NH$_3$ (Aq.) (95:5:0.5) to give a colorless foam (100 mg, 68%). The residue was suspended in ethanol (1 ml) and HCl-EtOH (6M, 1 ml) was added dropwise with stirring. The mixture was stirred at ambient temperature for 30 min. and the solid was collected and dried in vacuo at 60° C. to give the hydrochloride as a colorless solid. m.p.>250° C., [α]$_d$ −11.7° (c=0.098, MeOH).

Elementary analysis for C$_{29}$H$_{36}$N$_4$O$_5$S.HCl.0.55H$_2$O: Calculated; C 58.14; H 6.41; N 9.35%. Found; C 58.10; H 6.14; N 9.14%.

tography on silica gel, eluting with CH$_2$Cl$_2$/MeOH/NH$_3$ (Aq.) (96:4:0.4 increasing to 90:10:1) to give a colorless solid (182 mg, 82%). The residue was suspended in ethanol (5 ml) and HCl-EtOH (6M, 0.5 ml) was added dropwise with stirring. The mixture was stirred at ambient temperature for 1 h., then refrigerated over night. The solid was collected and recrystallized from ethanol/water (10 ml). The solid was collected and dried in vacuo at 5° C. to give the dihydrochloride as a colorless solid (139 mg), m.p. 303°–305° C. (Dec.), [α]$_d$ −33.0° (c=0.115, MeOH).

Elementary analysis for C$_{29}$H$_{37}$N$_5$O$_4$S.2HCl.0.85H$_2$O: Calculated; C 54.42; H 6.41; N 10.94%. Found; C 54.45; H 5.94; N 10.78%.

EXAMPLE 7

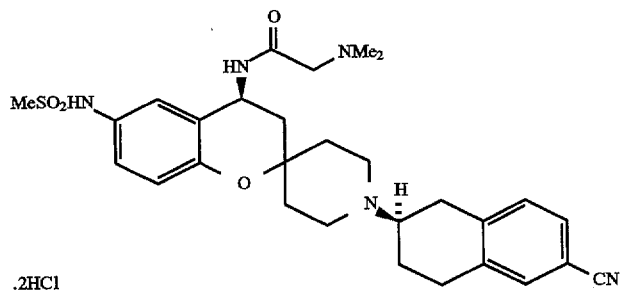

.2HCl (−)-(4S,2"R)-1'-[(6-Cyano-1,2,3,4-tetrahydronaphthalene)-2-yl]-3,4-dihydro-4-[2-(dimethylamino)acetamido]-6-methanesulfonamidospiro(2H-1-benzopyran-2,4'-piperidine)dihydrochloride 1-(3-Dimethylaminopropyl)-3-ethylcarbodiimide hydrochloride (84 mg, 0.44 mmol) was added to a stirred, cooled (0° C.) solution of (4S,2"R)-1'-[(6-cyano-1,2,3,4-tetrahydronaphthalene)-2-yl]-3,4-dihydro-6-methanesulfonamidospiro(2H-1-benzopyran-2,4'-piperidine)-4-amine (186 mg, 0.4 mmol), N,N-dimethylglycine (45 mg, 0.44 mmol) and 1-hydroxybenzotriazole (59 mg, 0.44 mmol) in DMF (4 ml). The mixture was stirred at room temperature for 22 h., poured into saturated aqueous sodium hydrogen carbonate (20 ml), diluted with water (10 ml) and extracted with ethyl acetate (3×20 ml). The combined organic fractions were washed with saturated aqueous sodium hydrogen carbonate (4×20 ml), dried (Na$_2$SO$_4$) and evaporated under reduced pressure. The residue was purified by flash column chroma-

EXAMPLE 8

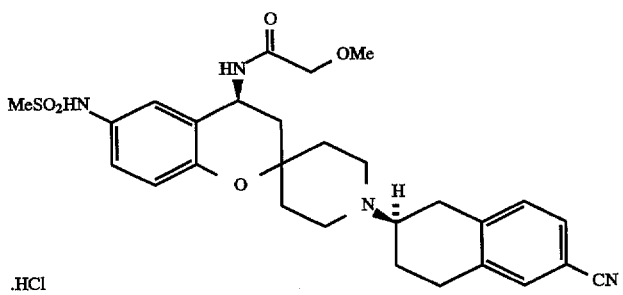

.HCl (−)-(4S,2"R)-1'-[(6-Cyano-1,2,3,4-tetrahydronaphthalene)-2-yl]-3,4-dihydro-4-[2-(methoxy)acetamido]-6-methanesulfonamidospiro (2H-1- benzopyran-2,4'-piperidine) hydrochloride 1-(3-Dimethylaminopropyl)-3-ethylcarbodiimide hydrochloride (84 mg, 0.44 mmol) was added to a stirred, cooled (0° C.) solution of (4S,2"R)-1'-[(6-cyano-1,2,3,4-tetrahydronaphthalene)-2-yl]-3,4-dihydro-6-methanesulfonamidospiro(2H-1-benzopyran-2,4'-piperidine)-4-amine (186 mg, 0.4 mmol), methoxyacetic acid (34 µl, 40 mg, 0.44 mmol) and 1-hydroxybenzotriazole (59 mg, 0.44 mmol) in DMF (4 ml). The mixture was stirred at room temperature for 20 h., poured into saturated aqueous sodium hydrogen carbonate (20 ml), diluted with water (10 ml) and extracted with ethyl acetate (3×20 ml). The combined organic fractions were washed with saturated aqueous sodium hydrogen carbonate (4×20 ml), dried (Na₂SO₄) and evaporated under reduced pressure. The residue was purified by flash column chromatography on silica gel, eluting with CH₂Cl₂/MeOH/NH₃ (Aq.) (96:4:0.4 increasing to 92:8:0.8) to give a colorless solid (177 mg, 82%). The residue was suspended in ethanol (5 ml) and HCl-EtOH (6M, 0.5 ml) was added dropwise with stirring. The mixture was stirred at ambient temperature for 1 h., then refrigerated over night.

The solid was collected and recrystallized from water (10 ml). The solid was collected and dried in vacuo at 50° C. to give the hydrochloride as a colorless solid (63 mg), m.p.>320° C., [α]$_d$ −26.4° (c=0.080, H₂O).

Elementary analysis for C$_{28}$H$_{34}$N$_4$O$_5$S.HCl: Calculated; C 58.48; H 6.13; N 9.74%. Found; C 58.40; H 5.90; N 9.71%.

EXAMPLE 9

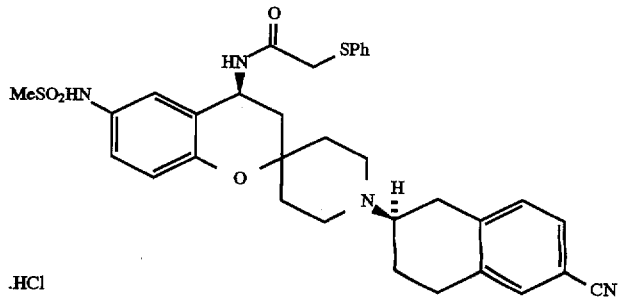

(−)-(4S,2"R)-1'-[(6-Cyano-1,2,3,4-tetrahydronaphthalene)-2-yl]-3,4-dihydro-6-methanesulfonamido-4-[2-(phenylthio)acetamido] spiro(2H-1-benzopyran-2,4'-piperidine) hydrochloride 1-(3-Dimethylaminopropyl)-3-ethylcarbodiimide hydrochloride (51 mg, 0.26 mmol) was added to a stirred, cooled (0° C.) solution of (4S,2"R)-1'-[(6-cyano-1,2,3,4-tetrahydronaphthalene)-2-yl]-3,4-dihydro-6-methanesulfonamidospiro(2H-1-benzopyran-2,4'-piperidine)-4-amine (44 mg, 0.24 mmol), thiophenoxyacetic acid (44 mg, 0.26 mmol) and 1-hydroxybenzotriazole (36 mg, 0.24 mmol) in DMF (3 ml). The mixture was stirred at room temperature for 20 h., poured into saturated aqueous sodium hydrogen carbonate (20 ml), diluted with water (10 ml) and extracted with ethyl acetate (3×20 ml). The combined organic fractions were washed with saturated aqueous sodium hydrogen carbonate (4×20 ml), dried (Na₂SO₄) and evaporated under reduced pressure. The residue was purified by flash column chromatography on silica gel, eluting with CH₂Cl₂/MeOH/NH₃ (Aq.) (96:4:0.4 increasing to 94:6:0.6) to give a colorless foam (95 mg, 64%). The residue was suspended in ethanol (5 ml) and HCl-EtOH (6M, 0.5 ml) was added dropwise with stirring. The mixture was stirred at ambient temperature for 1 h., then refrigerated over night. The solid was collected and dried in vacuo at 50° C. to give the hydrochloride as a colorless solid (84 mg), m.p. 271°–273° C., [α]$_d$ −23.8° (c=0.101, MeOH).

Elementary analysis for C$_{33}$H$_{36}$N$_4$O$_4$S$_2$.HCl: Calculated; C 60.67; H 5.71; N 8.58%. Found; C 60.63; H 6.03; N 8.62%.

EXAMPLE 10

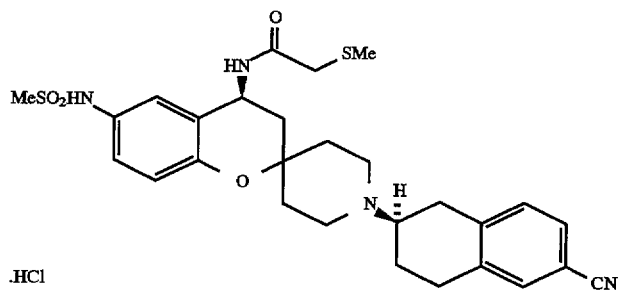

(−)-(4S,2"R)-1'-[(6-Cyano-1,2,3,4-tetrahydronaphthalene)-2-yl]-3,4-dihydro-6-methanesulfonamido-4-[2-(methylthio)acetamido] spiro(2H-1-benzopyran-2,4'-piperidine) hydrochloride 1-(3-Dimethylaminopropyl)-3-ethylcarbodiimide hydrochloride (109 mg, 0.57 mmol) was added to a stirred, cooled (0° C.) solution of (4S,2"R)-1'-[(6-cyano-1,2,3,4- tetrahydronaphthalene)-2-yl]-3,4-dihydro-6-methanesulfonamidospiro(2H-1-benzopyran-2,4'-piperidine)-4-amine (240 mg, 0.52 mmol), methylthioacetic acid (49 μl, 60 mg, 0.57 mmol) and 1-hydroxybenzotriazole (76 mg, 0.52 mmol) in DMF (5 ml). The mixture was stirred at room temperature for 24 h., poured into saturated aqueous sodium hydrogen carbonate (20 ml) diluted with water (10 ml) and extracted with ethyl acetate (3×20 ml). The combined organic fractions were washed with saturated aqueous sodium hydrogen carbonate (4×20 ml), dried (Na$_2$SO$_4$) and evaporated under reduced pressure. The residue was purified by flash column chromatography on silica gel, eluting with CH$_2$Cl$_2$/MeOH/NH$_3$ (Aq.) (96:4:0.4 increasing to 90:10:1) to give a colorless foam (149 mg, 52%). A sample (80 mg) was suspended in ethanol (5 ml) and HCl-EtOH (6M, 0.5 ml) was added dropwise with stirring. The mixture was stirred at ambient temperature for 1 h., then refrigerated over night. The solid was collected and dried in vacuo at 60° C. to give the hydrochloride as a colorless solid (80 mg), m.p. 304°–306° C., [α]$_d$ −19.2° (c=0.104, MeOH/10% H$_2$O).

Elementary analysis for C$_{28}$H$_{34}$N$_4$O$_4$S$_2$.HCl.0.6H$_2$O: Calculated; C 55.86: H 6.06; N 9.31%. Found; C 55.93; H 5.87; N 9.19%.

mmol) were added and the mixture was stirred at room temperature for 24 h., poured into saturated aqueous sodium hydrogen carbonate (20 ml), diluted with water (10 ml) and extracted with methylene chloride (3×20 ml). The combined organic fractions were dried (Na$_2$SO$_4$) and evaporated under reduced pressure. The residue was purified by flash column chromatography on silica gel, eluting with CH$_2$Cl$_2$/MeOH/NH$_3$ (Aq.) (94:6:0.6) to give a pale yellow solid (112 mg, 82%). The residue was dissolved in ethanol (5 ml) and HCl-EtOH (6M, 0.5 ml) was added dropwise with stirring. The mixture was stirred at ambient temperature for 1 h., then refrigerated over night. The solid was collected and dried in vacuo at 60° C. to give the hydrochloride as a colorless solid (91 mg), m.p. 275°–277° C., [α]$_d$ +4.4° (c=0.114, MeOH).

Elementary analysis for C$_{26}$H$_{32}$N$_4$O$_5$S$_2$.HCl.0.4H$_2$O: Calculated; C 53.07; H 5.79; N 9.52%. Found; C 53.05; H 5.64; N 9.58%.

EXAMPLE 11

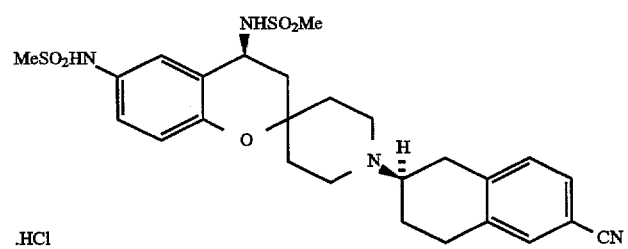

(+)-(4S,2"R)-1'-[(6-Cyano-1,2,3,4-tetrahydronaphthalene)-2-yl]-3,4-dihydro-4,6-bis(methanesulfonamido)spiro(2H-1-benzopyran-2,4'-piperidine)hydrochloride Methanesulfonyl chloride (19 μl, 29 mg, 0.28 mmol) was added to a stirred, cooled (0° C.) solution of (4S,2"R)-1'-[(6-cyano-1,2,3,4-tetrahydronaphthalene)-2-yl]-3,4-dihydro-6-methanesulfonamidospiro(2H-1-benzopyran-2,4'-piperidine)-4-amine (116 mg, 0.25 mmol) in methylene chloride (5 ml). The mixture was stirred at __° C. for 1 h., then at room temperature for 19 h. Pyridine (40 μl, 40 mg, 0.5 mmol) and methanesulfonyl chloride (19 μl, 29 mg, 0.28

EXAMPLE 12

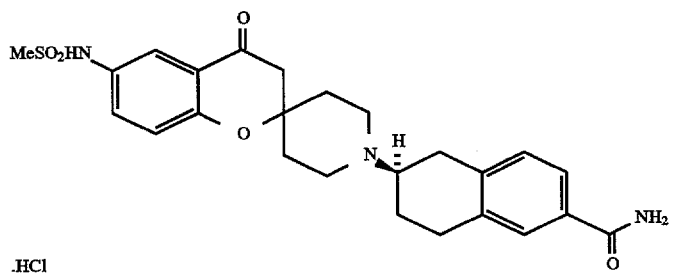

(+)-(2"R)-1'-[(6-Aminocarbonyl-1,2,3,4-tetrahydronaphthalene)-2-yl]-3,4-dihydro-6-methanesulfonamidospiro(2H-1-benzopyran-2,4'-piperidine)-4-one hydrochloride (+)-(2"R)-1'-[(6-Cyano-1,2,3,4-tetrahydronaphthalene)-2-yl]-3,4-dihydro-6-methanesulfonamidospiro(2H-1- benzopyran-2,4'-piperidine)-4-one 232 mg, 0.5 mmol) was added to a cooled (0° C.) mixture of concentrated sulfuric acid (3.5 ml) and water (1.5 ml). The mixture was stirred at room temperature for 45 h., then at 50° C. for 12 h. The mixture was cooled and poured onto ice (20 g). The mixture was heated to give a clear yellow solution which was allowed to cool with stirring to room temperature. The mixture was refrigerated overnight and the solid was collected and dried in vacuo to give (+)-(2"R)-1'-[(6-aminocarbonyl-1,2,3,4-tetrahydronaphthalene)-2-yl]-3,4-dihydro-6-methanesulfonamidospiro(2H-1-benzopyran-2,4'-piperidine)-4-one hydrogen sulfate. Saturated aqueous sodium hydrogen carbonate (20 ml) and water (20 ml) were added and the mixture was extracted with methylene chloride (10×20 ml). The combined organic fractions were dried (Na$_2$SO$_4$) and evaporated under reduced pressure. The residue was redissolved in THF (20 ml) silica gel was added and the solvent was evaporated under reduced pressure. The residue was purified by flash column chromatography on silica gel, eluting with CH$_2$Cl$_2$/MeOH/NH$_3$ (Aq.) (94:6:0.6 increasing to 90:10:1) and the residue was triturated with methanol (5 ml) to give a pale yellow solid (175 mg, 72%). The residue was suspended in ethanol (5 ml) and HCl-EtOH (6M, 0.5 ml) was added dropwise with stirring. The mixture was stirred at ambient temperature for 1 h., then refrigerated over night. The solid was collected and recrystallized from water (10 ml). The solid was collected and dried in vacuo at 50° C. to give the hydrochloride as an off-white solid (147 mg), m.p.>300° C., [α]$_d$ +46.0° (c=0.118, MeOH/5% H$_2$O).

Elementary analysis for C$_{25}$H$_{29}$N$_3$O$_5$S.HCl: Calculated; C 57.74; H 5.81; N 8.08%. Found; C 57.53; H 6.02; N 8.18%.

EXAMPLE 13

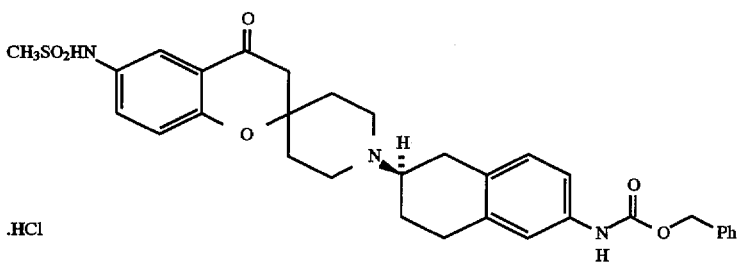

(+)-(2"R)-1'-{[6-(Benzyloxy)carboxamido-1,2,3,4-tetrahydronaphthalene]-2-yl}-3,4-dihydro-6-methanesulfonamidospiro(2H-1-benzopyran-2,4'-piperidine)-4-one hydrochloride Iodobenzene diacetate (101 mg, 0.32 mmol) was added to a stirred, heated (40° C.) solution of (+)-(2"R)-1'-[(6-aminocarbonyl-1,2,3,4-tetrahydronaphthalene)-2-yl]-3,4-dihydro-6-methanesulfonamidospiro(2H-1-benzopyran-2,4'-piperidine)-4-one hydrogen sulfate (174 mg, 0.3 mmol) and 1,8-diazabicyclo[5.4.0]undec-7-ene (0.359 ml, 365 mg, 2.4 mmol) in benzyl alcohol (3 ml). The mixture was stirred at 40° C. for 20 min., poured into saturated aqueous sodium hydrogen carbonate (20 ml), diluted with water (10 ml) and extracted with ethyl acetate (3×20 ml). The combined organic fractions were washed with aqueous sodium thiosulfate (5%, 20 ml), saturated aqueous sodium hydrogen carbonate (20 ml) and brine (20 ml), dried (Na$_2$SO$_4$) and evaporated under reduced pressure. The residue was purified by flash column chromatography on silica gel, eluting with CH$_2$Cl$_2$/MeOH/NH$_3$ (Aq.) (99:1:0.1 increasing to 96:4:0.4) to give a yellow glass (132 mg, 75%). The residue was dissolved in ethanol (5 ml) and HCl-EtOH (6M, 0.5 ml) was added dropwise with stirring. The mixture was heated to reflux, filtered, allowed to cool to room temperature and refrigerated over night. The solid was collected and dried in vacuo at 50° C. to give the hydrochloride as a pale yellow solid (116 mg), m.p. 181°–183° C., [α]$_d$ +32.6° (c=0.172, MeOH).

Elementary analysis for C$_{32}$H$_{35}$N$_3$O$_6$S.HCl.H$_2$O: Calculated; C 59.66; H 5.95; N 6.52%. Found; C 59.44; H 5.84; N 6.61%.

EXAMPLE 14

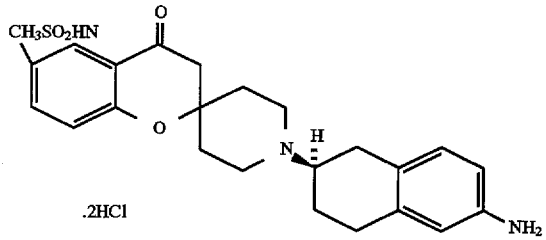

(+)-(2"R)-1'-[(6-Amino-1,2,3,4-tetrahydronaphthalene)-2-yl]-3,4-dihydro-6-methanesulfonamidospiro(2H-1-benzopyran-2,4'-piperidine)-4-one dihydrochloride Ammonium formate (650 mg, 10.3 mmol) was added to a suspension of (+)-(2"R)-1'-{[6-(benzyloxy)carboxamido-1,2,3,4-tetrahydronaphthalene]-2-yl}-3,4-dihydro-6-methanesulfonamidospiro(2H-1-benzopyran-2,4'-piperidine)-4-one (1.21 g, 2.06 mmol) in methanol (50 ml) and argon was bubbled through the mixture for 15 min. Palladium on carbon (10%, 200 mg) was added and the mixture was stirred under hydrogen (1 Atm.) for 6 h. The mixture was filtered through celite, washing with methanol and the solvent was evaporated under reduced pressure. Saturated aqueous sodium hydrogen carbonate (50 ml) and water (20 ml) were added and the mixture was extracted with methylene chloride (3×50 ml). The combined organic fractions were dried (Na$_2$SO$_4$) and evaporated under reduced pressure. The residue was purified by flash column chromatography on silica gel, eluting with CH$_2$Cl$_2$/MeOH/NH$_3$ (Aq.) (96:4:0.4) to give a yellow foam (927 mg, 99%).

A sample (273 mg) was dissolved in ethanol (5 ml) and HCl-EtOH (6M, 0.5 ml) was added dropwise with stirring. The mixture was stirred at ambient temperature for 1 h. then refrigerated overnight. The solid was collected and dried in vacuo at 50° C. to give the dihydrochloride as an off-white solid (241 mg), m.p. 250°–252° C. (Dec.), $[\alpha]_d$ +34.3° (c=0.186, MeOH).

Elementary analysis for $C_{24}H_{29}N_3O_4S.2HCl.0.25EtOH.1.95H_2O$: Calculated; C 51.16; H 6.38; N 7.31%. Found; C 51.62; H 5.89; N 6.81%.

EXAMPLE 15

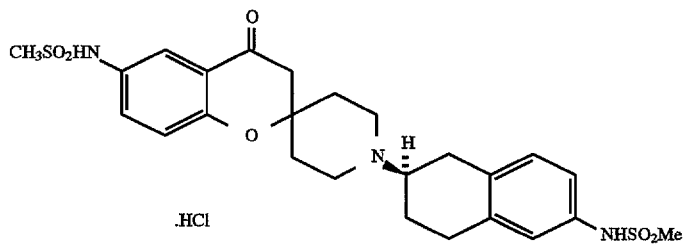

(+)-(2"R)-3,4-Dihydro-6-methanesulfonamido-1'-[(6-methanesulfonamido-1,2,3,4-tetrahydronaphthalene)-2-yl]spiro(2H-1-benzopyran-2,4'-piperidine)-4-one hydrochloride Methanesulfonyl chloride (51 µl, 76 mg, 0.66 mmol) was added to a stirred, cooled (0° C.) solution of (+)-(2"R)-1'-[(6-amino-1,2,3,4-tetrahydronaphthalene)-2-yl]-3,4-dihydro-6-methanesulfonamidospiro(2H-1-benzopyran-2,4'-piperidine)-4-one (273 mg, 0.6 mmol) and pyridine (97 µl, 95 mg, 1.2 mmol) in methylene chloride (5 ml). The mixture was stirred at 0° C. for 1 h., then at room temperature for 15 h. Methanol (10 ml), saturated aqueous sodium hydrogen carbonate (20 ml) and water (20 ml) were added and the mixture was extracted with methylene chloride (3×20 ml). The combined organic fractions were dried ($Na_2SO_4$) and evaporated under reduced pressure, adsorbing onto silica gel. The residue was purified by flash column chromatography on silica gel, eluting with $CH_2Cl_2$/MeOH/$NH_3$ (Aq.) (98:2:0.2 increasing to 92:8:0.8) to give a pale yellow foam (278 mg, 87%). The residue was suspended in ethanol (5 ml) and HCl-EtOH (6M, 0.5 ml) was added dropwise with stirring. The mixture was stirred at ambient temperature for 1 h. then refrigerated overnight. The solid was collected and dried in vacuo at 50° C. to give the hydrochloride as a white solid (236 mg), m.p. 283°–285° C. (Dec.), $[\alpha]_d$ +35.0° (c=0.103, MeOH/5% $H_2O$).

Elementary analysis for $C_{25}H_{31}N_3O_6S_2.HCl.0.5H_2O$: Calculated; C 51.84; H 5.74; N 7.26%. Found; C 52.04; H 5.51; N 7.09%.

EXAMPLE 16

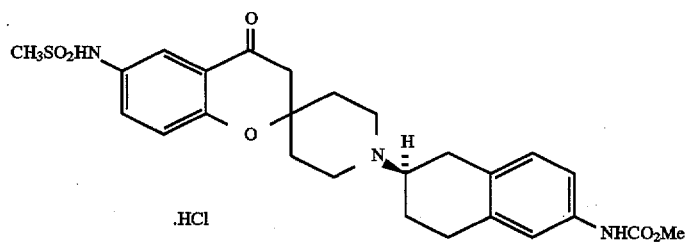

(+)-(2"R)-3,4-Dihydro-6-methanesulfonamido-1'-{[6-(methoxy)carboxamido-1,2,3,4-tetrahydronaphthalene]-2-yl}spiro(2H-1-benzopyran-2,4'-piperidine)-4-one hydrochloride Methyl chloroformate (34 µl, 42 mg, 0.44 mmol) was added to a stirred, cooled (0° C.) solution of (+)-(2"R)-1'-[(6-amino-1,2,3,4-tetrahydronaphthalene)-2-yl]-3,4-dihydro-6-methanesulfonamidospiro(2H-1-benzopyran-2,4'-piperidine)-4-one (182 mg, 0.4 mmol) and pyridine (65 µl, 63 mg, 0.8 mmol) in methylene chloride (4 ml). The mixture was stirred at 0° C. for 1 h., then at room temperature for 20 h. Saturated aqueous sodium hydrogen carbonate (20 ml) and water (5 ml) were added and the mixture was extracted with methylene chloride (3×20 ml). The combined organic fractions were dried ($Na_2SO_4$) and evaporated under reduced pressure. The residue was purified by flash column chromatography on silica gel, eluting with $CH_2Cl_2$/MeOH/$NH_3$ (Aq.) (98:2:0.2 increasing to 94:6:0.6) to give a yellow foam (151 mg, 74%). A sample (70 mg) was dissolved in ethanol (2 ml) and HCl-EtOH (6M, 0.2 ml) was added dropwise with stirring. The mixture was stirred at ambient temperature for 1 h. then refrigerated overnight. The solid was collected and dried in vacuo at 60° C. to give the hydrochloride as a white solid (59 mg), m.p. 258°–260° C. (Dec.), $[\alpha]_d$ +38.8° (c=0.126, MeOH/5% $H_2O$).

Elementary analysis for $C_{26}H_{31}N_3O_6S \cdot HCl$: Calculated; C 56.77; H 5.86; N 7.64%. Found; C 56.42; H 5.93; N 7.50%.

EXAMPLE 17

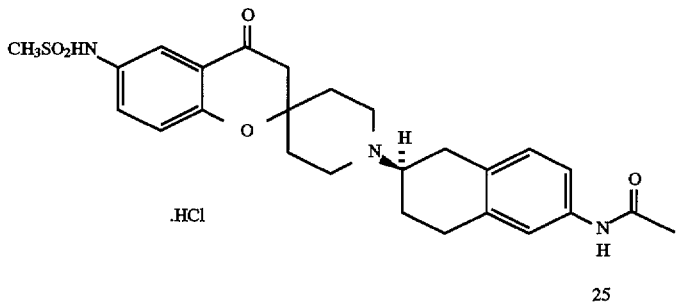

(+)-(2"R)-1'-[(6-Acetamido-1,2,3,4-tetrahydronaphthalene)-2-yl]-3,4-dihydro-6-methanesulfonamidospiro(2H-1-benzopyran-2,4'-piperidine)-4-one hydrochloride Acetic anhydride (42 μl, 45 mg, 0.44 mmol) was added to a stirred, cooled (0° C.) solution of (+)-(2"R)-1'-[(6-amino-1,2,3,4-tetrahydronaphthalene)-2-yl]-3,4-dihydro-6-methanesulfonamidospiro(2H-1-benzopyran-2,4'-piperidine)-4-one (182 mg, 0.4 mmol) in methylene chloride (4 ml). The mixture was stirred at 0° C. for 1 h., then at room temperature for 20 h. Saturated aqueous sodium hydrogen carbonate (20 ml) and water (5 ml) were added and the mixture was extracted with methylene chloride (3×20 ml). The combined organic fractions were dried ($Na_2SO_4$) and evaporated under reduced pressure. The residue was purified by flash column chromatography on silica gel, eluting with $CH_2Cl_2$/MeOH/$NH_3$ (Aq.) (96:4:0.4 increasing to 90:10:1) to give a yellow foam (170 mg. 86%). A sample (80 mg) was suspended in ethanol (2 ml) and HCl-EtOH (6M, 0.2 ml) was added dropwise with stirring. The mixture was stirred at ambient temperature for 1 h. then refrigerated overnight. The solid was collected and dried in vacuo at 60° C. to give the hydrochloride as a white solid (71 mg), m.p. 280°–282° C. (Dec.), $[\alpha]_d$ +41.2° (c=0.116, MeOH).

Elementary analysis for $C_{26}H_{31}N_3O_5S \cdot HCl \cdot 0.5H_2O$: Calculated; C 57.50; H 6.12; N 7.74%. Found; C 57.67; H 6.26; N 7.61%.

EXAMPLE 18

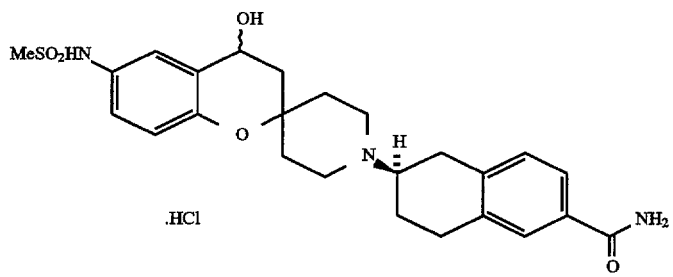

(+)-(4RS,2"R)-1'-[(6-Aminocarbonyl-1,2,3,4-tetrahydronaphthalene)-2-yl]-3,4-dihydro-6-methanesulfonamidospiro(2H-1-benzopyran-2,4'-piperidine)-4-ol hydrochloride Sodium borohydride (15 mg, 0.4 mmol) was added to a stirred, cooled (0° C.) suspension of (+)-(2"R)-1'-[(6-aminocarbonyl-1,2,3,4-tetrahydronaphthalene)-2-yl]-3,4-dihydro-6-methanesulfonamido-spiro(2H-1-benzopyran-2,4'-piperidine)-4-one hydrogen sulfate (232 mg, 0.4 mmol) in ethanol (5 ml). The mixture was stirred at 0° C. for 1 h., then at room temperature for 136 h., adding further sodium borohydride (10 portions of 15 mg, 0.4 mmol). Saturated aqueous sodium hydrogen carbonate (20 ml) and water (10 ml) were added and the mixture was extracted with methylene chloride (10×20 ml). The combined organic fractions were dried ($Na_2SO_4$) and evaporated under reduced pressure. The residue was purified by flash column chromatography on silica gel, eluting with $CH_2Cl_2$/MeOH/$NH_3$ (Aq.) (92:8:0.8 increasing to 86:14:1.4) to give an off-white solid (193 mg, 99%). The residue was dissolved in ethanol (5 ml), cooled to 0° C. and HCl-EtOH (6M, 0.5 ml) was added dropwise with stirring. The mixture was stirred at ambient temperature for 1 h. then refrigerated overnight. The solid was collected and dried in vacuo at 35° C. to give the hydrochloride as a white solid (174 mg). m.p. 265°–267° C., $[\alpha]_d$ +43.4° (c=0.110, MeOH).

Elementary analysis for $C_{25}H_{31}N_3O_5S.HCl.0.75H_2O$: Calculated; C 56.06; H 6.30; N 7.85%. Found; C 56.34; H 6.69; N 7.51%.

EXAMPLE 19

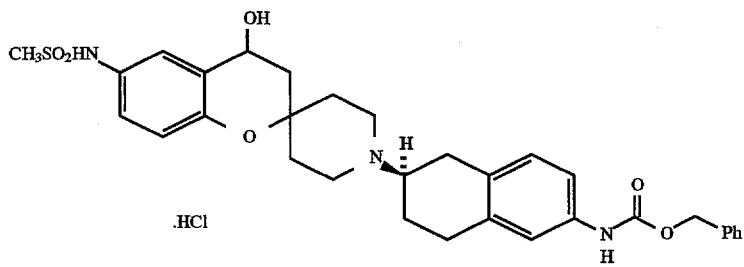

.HCl (+)-(4RS,2"R)-1'-{[6-(Benzyloxy)carboxamido-1,2,3,4-tetrahydronaphthalene]-2-yl}-3,4-dihydro-6-methanesulfonamidospiro(2H-1-benzopyran-2,4'-piperidine)-4-ol hydrochloride Sodium borohydride (19 mg, 0.5 mmol) was added to a stirred, cooled (0° C.) suspension of (+)-(2"R)-1'-{[6-(benzyloxy)carbox-amido-1,2,3,4-tetrahydronaphthalene]-2-yl}-3,4-dihydro-6-methanesulfon-amidospiro(2H-1-benzopyran-2,4'-piperidine)-4-one (147 mg, 0.25 mmol) in ethanol (1 ml). The mixture was stirred at 0° C. for 1 h., then at room temperature for 16 h. Saturated aqueous sodium hydrogen carbonate (50 ml) and water (20 ml) were added and the mixture was extracted with methylene chloride (3×50 ml). The combined organic fractions were dried ($Na_2SO_4$) and evaporated under reduced pressure. The residue was purified by flash column chromatography on silica gel, eluting with $CH_2Cl_2$/MeOH/$NH_3$ (Aq.) (96:4:0.4 increasing to 90:10:1) to give a colorless foam (115 mg, 78%). The residue was dissolved in ethanol (5 ml), cooled to 0° C. and HCl-EtOH (6M, 0.5 ml) was added dropwise with stirring. The mixture was stirred at ambient temperature for 1 h. then refrigerated overnight. The solid was collected and dried in vacuo at 35° C. to give the hydrochloride as an off-white solid (90 mg), m.p. 163°–165° C., $[\alpha]_d$ +36.1° (c=0.133, MeOH).

Elementary analysis for $C_{32}H_{37}N_3O_6S.HCl.H_2O$: Calculated; C 59.47; H 6.24; N 6.50%. Found; C 59.47; H 6.04; N 6.69%.

EXAMPLE 20

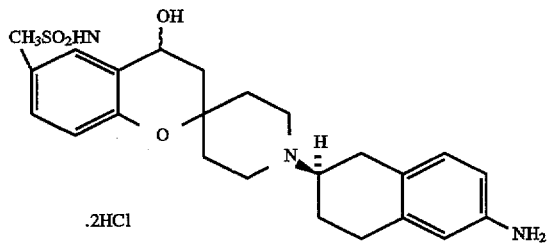

.2HCl (+)-(4RS,2"R)-1'-[(6-Amino-1,2,3,4-tetrahydronaphthalene)-2-yl]-3,4-dihydro-6-methanesulfonamidospiro(2H-1-benzopyran-2,4'-piperidine)-4-ol dihydrochloride Sodium borohydride (15 mg, 0.4 mmol) was added to a stirred, cooled (0° C.) suspension of (+)-(2"R)-1'-[(6-amino-1,2,3,4-tetrahydronaphthalene)-2-yl]-3,4-dihydro-6-methanesulfonamidospiro(2H-1-benzopyran-2,4'-piperidine)-4-one (106 mg, 0.2 mmol) in ethanol (2 ml). The mixture was stirred at 0° C. for 1 h., then at room temperature for 6 h. The mixture was cooled to 0° C. and further sodium borohydride (15 mg, 0.4 mmol) was added. The mixture was stirred at 0° C. for 1 h., then at room temperature for 16 h. Saturated aqueous sodium hydrogen carbonate (20 ml) and water (50 ml) were added and the mixture was extracted with methylene chloride (3×20 ml). The combined organic fractions were dried ($Na_2SO_4$) and evaporated under reduced pressure. The residue was purified by flash column chromatography on silica gel, eluting with $CH_2Cl_2$/MeOH/$NH_3$ (Aq.) (96:4:0.4 increasing to 88:12:1.2) to give a colorless solid (91 mg, 100%). The residue was dissolved in ethanol (5 ml), cooled to 0° C. and HCl-EtOH (6M, 0.5 ml) was added dropwise with stirring. The mixture was stirred at ambient temperature for 1 h. then refrigerated overnight. The solid was collected and dried in vacuo at 35° C. to give the dihydrochloride as an off-white solid (70 mg), m.p. 242°–244° C., $[\alpha]_d$ +40.6° (c=0.106, MeOH).

Elementary analysis for $C_{24}H_{31}N_3O_4S.2HCl.1.75H_2O$: Calculated; C 51.28; H 6.55; N 7.48%. Found; C 51.26; H 6.57; N 6.59%.

EXAMPLE 21

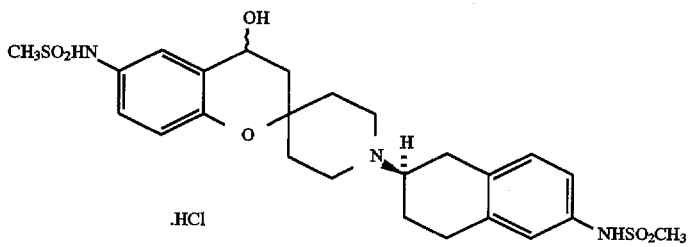

(+)-(4RS,2"R)-3,4-Dihydro-6-methanesulfonamido-1'-[(6-methanesulfonamido-1,2,3,4-tetrahydronaphthalene)-2-yl]spiro(2H-1-benzopyran-2,4'-piperidine)-4-ol hydrochloride Sodium borohydride (15 mg, 0.4 mmol) was added to a stirred, cooled (0° C.) suspension of (+)-(2"R)-3,4-dihydro-6-methanesulfonamido-1'-[(6-methanesulfonamido-1,2,3,4-tetrahydronaphthalene)-2-yl]spiro(2H-1-benzopyran-2,4'-piperidine)-4-one (114 mg, 0.22 mmol) in ethanol (2 ml). The mixture was stirred at 0° C. for 1 h., then at room temperature for 6 h. The mixture was cooled to 0° C. and further sodium borohydride (15 mg, 0.4 mmol) was added. The mixture was stirred at 0° C. for 1 h., then at room temperature for 16 h. Saturated aqueous sodium hydrogen carbonate (20 ml) and water (5 ml) were added and the mixture was extracted with methylene chloride (3×20 ml). The combined organic fractions were dried ($Na_2SO_4$) and evaporated under reduced pressure. The residue was purified by flash column chromatography on silica gel, eluting with $CH_2Cl_2$/MeOH/$NH_3$ (Aq.) (96:4:0.4 increasing to 88:12:1.2) to give a colorless foam (96 mg, 90%). The residue was dissolved in ethanol (5 ml), cooled to 0° C. and HCl-EtOH (6M, 0.5 ml) was added dropwise with stirring. The mixture was stirred at ambient temperature for 1 h. then refrigerated overnight. The solid was collected and dried in vacuo at 35° C. to give the hydrochloride as a colorless solid (77 mg), m.p. 267°–269° C. $[\alpha]_d$ +40.4° (c=0.106, MeOH).

Elementary analysis for $C_{25}H_{33}N_3O_6S_2$·HCl: Calculated; C 52.48; H 5.99; N 7.34%. Found; C 52.35; H 6.00; N 7.25%.

(+)-(4RS,2"R)-3,4-Dihydro-6-methanesulfonamido-1'-{[6-(methoxy)carboxamido-1,2,3,4-tetrahydronaphthalene]-2-yl}spiro(2H-1-benzopyran-2,4'-piperidine)-4-ol hydrochloride Sodium borohydride (12 mg, 0.31 mmol) was added to a stirred, cooled (0° C.) suspension of (+)-(2"R)-3,4-dihydro-6-methanesulfonamido-1'-[(6-methanesulfonamido-1,2,3,4-tetrahydronaphthalene)-2-yl]spiro(2H-1-benzopyran-2,4'-piperidine)-4-one (80 mg, 0.16 mmol) in ethanol (2 ml). The mixture was stirred at 0° C. for 1 h., then at room temperature for 23 h. Saturated aqueous sodium hydrogen carbonate (20 ml) and water (5 ml) were added and the mixture was extracted with methylene chloride (3×20 ml). The combined organic fractions were dried ($Na_2SO_4$) and evaporated under reduced pressure. The residue was purified by flash column chromatography on silica gel, eluting with $CH_2Cl_2$/MeOH/$NH_3$ (Aq.) (96:4:0.4 increasing to 88:12:1.2) to give a colorless glass (78 mg, 97%). The residue was dissolved in ethanol (2 ml) cooled to 0° C. and HCl-EtOH (6M, 0.2 ml) was added dropwise with stirring. The mixture was stirred at ambient temperature for 1 h. then refrigerated overnight. The solid was collected and dried in vacuo at 35° C. to give the hydrochloride as a colorless solid (51 mg), m.p. 194°–196° C., $[\alpha]_d$ +39.8° (c=0.118, MeOH).

Elementary analysis for $C_{26}H_{33}N_3O_6S$·HCl·$H_2O$: Calculated; C 54.77; H 6.37; N 7.37%. Found; C 55.15; H 6.47; N 6.91%.

EXAMPLE 22

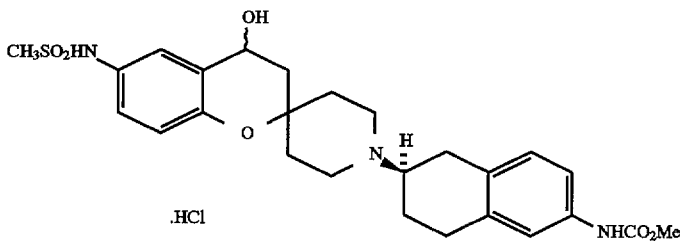

EXAMPLE 23

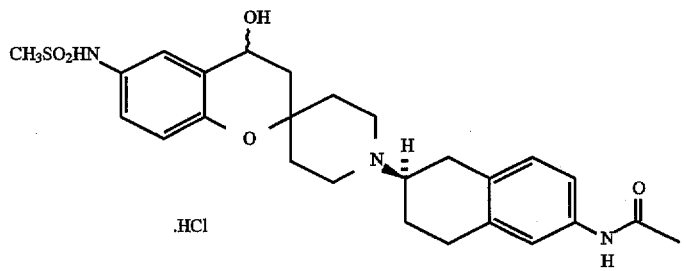

(+)-(4RS,2"R)-1'-[(6-Acetamido-1,2,3,4-tetrahydronaphthalene)-2-yl]-3,4-dihydro-6-methanesulfonamidospiro(2H-1-benzopyran-2,4'-piperidine)-4-ol hydrochloride Sodium borohydride (14 mg, 0.36 mmol) was added to a stirred, cooled (0° C.) suspension of (+)-(2"R)-1'-[(6-acetamido-1,2,3,4-tetrahydronaphthalene)-2-yl]-3,4-dihydro-6-methanesulfonamidospiro(2H-1-benzopyran-2,4'-piperidine)-4-one (90 mg, 0.18 mmol) in ethanol (2 ml). The mixture was stirred at 0° C. for 1 h., then at room temperature for 23 h. Saturated aqueous sodium hydrogen carbonate (20 ml) and water (5 ml) were added and the mixture was extracted with methylene chloride (3×20 ml). The combined organic fractions were dried ($Na_2SO_4$) and evaporated under reduced pressure. The residue was purified by flash column chromatography on silica gel, eluting with $CH_2Cl_2$/MeOH/$NH_3$ (Aq.) (96:4:0.4 increasing to 88:12:1.2) to give a colorless foam (82 mg, 92%). The residue was dissolved in ethanol (2 ml), cooled to 0° C. and HCl-EtOH (6M, 0.2 ml) was added dropwise with stirring. The mixture was stirred at ambient temperature for 1 h. then refrigerated overnight. The solid was collected and dried in vacuo at 35° C. to give the hydrochloride as a colorless solid (54 mg), m.p. 236°–238° C., $[\alpha]_d$ +43.7° (c=0.142, MeOH).

Elementary analysis for $C_{26}H_{33}N_3O_5S.HCl.H_2O$: Calculated; C 56.35; H 6.55; N 7.58%. Found; C 55.88; H 6.14; N 7.84%.

EXAMPLE 24

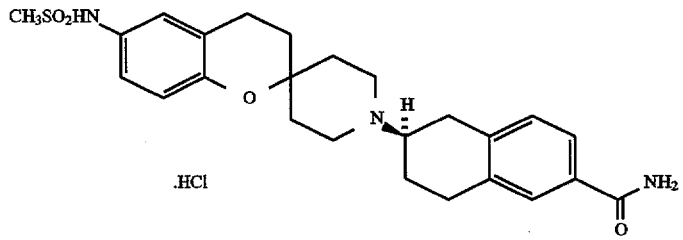

1'-[(6-Aminocarbonyl-1,2,3,4-tetrahydronaphthalene)-2-yl]-3,4-dihydro-6-methanesulfonamidospiro(2H-1-benzopyran-2,4'-piperidine)hydrochloride A mixture of (+)-(2"R)-1'-[(6-cyano-1,2,3,4-tetrahydronaphthalene)-2-yl]-3,4-dihydro-6-methanesulfonamidospiro(2H-1-benzopyran-2,4'-piperidine) (2.57 g, 5.7 mmol) and potassium hydroxide (0.96 g, 17.1 mmol) in ethanol (60 ml) was heated under reflux for 72 h., cooled and the solvent was evaporated under reduced pressure. The residue was purified by flash column chromatography on silica gel, eluting with $CH_2Cl_2$/MeOH/$NH_3$ (Aq.) (94:6:0.6 increasing to 90:10:1) to give an off-white solid (1.89 g, 71%). The residue was recrystallized from methanol (500 ml) to give a colorless solid (1.18 g). A sample (150 mg) was suspended in ethanol (5 ml), cooled to 0° C. and HCl-EtOH (6M, 0.5 ml) was added dropwise with stirring. The mixture was stirred at ambient temperature for 1 h. then refrigerated overnight. The solid was collected and dried in vacuo at 50° C. to give the hydrochloride as a colorless solid (150 mg), m.p.>300° C., $[\alpha]_d$ +42.1° (c=0.171, MeOH).

Elementary analysis for $C_{25}H_{31}N_3O_4S.HCl.0.75H_2O$: Calculated; C 57.79; H 6.50; N 8.09%. Found; C 57.83; H 6.15; N 8.05%.

EXAMPLE 25

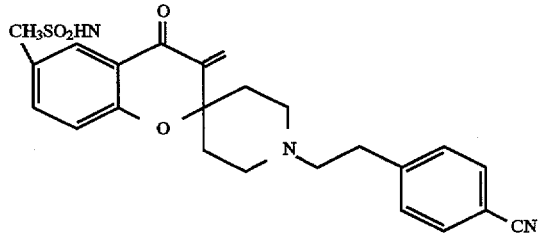

1'-[2-(4-Cyanophenyl)ethyl]-3,4-dihydro-6-methanesulfonamido-3-methylenespiro(2H-1-benzopyran-2,4'-piperidine)-4-one N,N,N',N'-Tetramethyldiaminomethane (1.36 ml, 1.02 g, 10 mmol) was added to a solution of 1'-[2-(4-cyanophenyl)ethyl]-3,4-dihydro-6-methanesulfonamidospiro(2H-1-benzopyran-2,4'-piperidine)-4-one (2.20 g, 5 mmol) and acetic acid (1.14 ml, 1.20 g, 20 mmol) in THF (40 ml) and the mixture was heated under reflux for 24 h. Further N,N,N',N'-tetramethyldiaminomethane (1.36 ml, 1.02 g, 10 mmol) and acetic acid (1.14 ml, 1.20 g, 20 mmol) were added and the mixture was heated under reflux for 6 h, cooled and poured into saturated aqueous sodium hydrogen carbonate (150 ml), diluted with water (50 ml) and extracted with methylene chloride (3×150 ml). The combined organic fractions were dried (Na₂SO₄) and evaporated under reduced pressure. Toluene (600 ml) was added and the volume was reduced by distillation to 300 ml. Further toluene (300 ml) was added and the volume was reduced by distillation to 300 ml. The mixture was allowed to cool with stirring to room temperature then refrigerated overnight. The solid was collected and dried in vacuo to give the ketone as a yellow solid (1.98 g, 88%).

$\delta_H$H(CDCl₃) 7.77 (1H, d, J 2.9 Hz), 7.59 (3H, m), 7.34 (2H, d, J 8.1 Hz), 7.04 (1H, d, J 8.8 Hz), 6.65 (1H, br s), 6.42 (1H, s), 5.67 (1H, s), 3.02 (3H, s), 3.00–2.40 (8H, m), and 2.20–1.50 (4H, m).

EXAMPLE 26

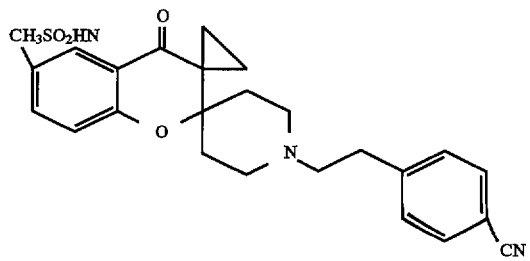

1"-[2-(4-Cyanophenyl)ethyl]-6'-methanesulfonamidodispiro[cyclopropane-1,3'(4'H)-[2H-1]benzopyran-2',4"-piperidine]-4'-one Sodium hydride (60% dispersion in mineral oil, 96 mg, 2.4 mmol) was added with water bath cooling to a solution of trimethylsulfoxonium iodide (440 mg, 2.0 mmol) in DMSO (30 ml). The mixture was stirred at room temperature for 20 min. and 1'-[2-(4-cyanophenyl)ethyl]-3,4-dihydro-6-methanesulfonamido-3-methylenespiro(2H-1-benzopyran-2,4'-piperidine-one (451 mg, 1.0 mmol) was added. The mixture was stirred at room temperature for 1 h., poured into saturated aqueous sodium hydrogen carbonate (200 ml), diluted with water (50 ml) and extracted with ethyl acetate (3×200 ml). The combined organic fractions were washed with saturated aqueous sodium hydrogen carbonate (4×200 ml), dried (Na₂SO₄) and evaporated under reduced pressure. The residue was purified by flash column chromatography on silica gel, eluting with CH₂Cl₂/MeOH/NH₃ (Aq.) (99:1:0.1 increasing to 96:4:0.4) to give the ketone as a colorless solid (390 mg, 84%).

$\delta_H$(d₆-DMSO) 7.64 (1H, d, J 2.8 Hz), 7.58 (2H, d, J 8.1 Hz), 7.55 (1H, dd, J 8.8, 2.8 Hz), 7.30 (2H, d, J 8.1 Hz), 7.06 (1H, d, J 8.8 Hz), 6.38 (1H, br s), 3.00 (3H, s), 2.83 (2H, m), 2.78 (2H, m), 2.64 (2H, m), 2.42 (2H, m), 1.99 (2H, m), 1.54 (2H, m), 1.38 (2H, m), and 1.10 (2H, m).

EXAMPLE 27

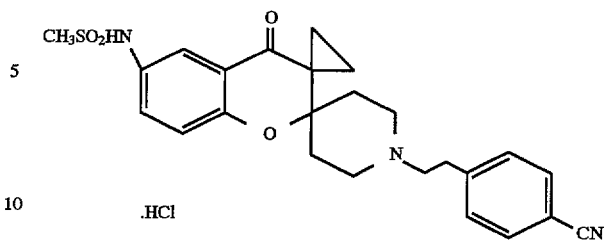

1"-[2-(4-Cyanophenyl)ethyl]-6'-methanesulfonamidodispiro[cyclopropane-1,3'(4'H)-[2H-1]benzopyran-2',4"-piperidine]-4'-one hydrochloride 1"-[2-(4-Cyanophenyl)ethyl]-6'-methanesulfonamidodispiro-[cyclopropane-1,3'(4'H)-[2H-1]benzopyran-2',4"-piperidine]-4'-one (250 mg, 0.54 mmol) was suspended in ethanol (10 ml) and HCl-EtOH (6M, 1 ml) was added dropwise with stirring. The mixture was stirred at ambient temperature for 1 h., then refrigerated over night. The solid was collected and dried in vacuo at 50° C. to give the hydrochloride as a colorless solid (257 mg, 95%), m.p. 272°–274° C.

Elementary analysis for C₂₅H₂₇N₃O₄S.HCl.0.35H₂O: Calculated; C 59.06; H 5.69; N 8.27%. Found; C 59.08; H 5.75; N 8.12%.

EXAMPLE 28

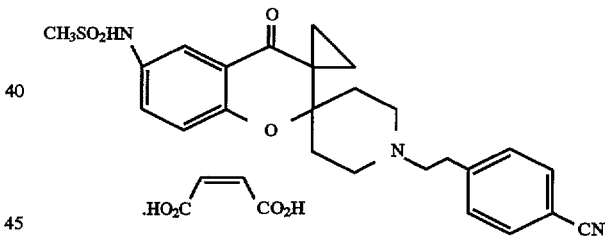

1"-[2-(4-Cyanophenyl)ethyl]-6'-methanesulfonamidodispiro[cyclopropane-1,3'(4'H)-[2H-1]benzopyran-2',4"-piperidine]-4'-one maleate 1"-[2-(4-Cyanophenyl)ethyl]-6'-methanesulfonamidodispiro[cyclopropane-1,3'(4'H)-[2H-1]benzopyran-2',4"-piperidine]-4'-one (93 mg, 0.2 mmol) was suspended in ethanol (5 ml) and maleic acid (23.2 mg, 0.2 ml) was added. The mixture was stirred at ambient temperature for 1 h., then the solvent was evaporated under reduced pressure. The residue was recrystallized from EtOH/H₂O (20:1, 10 ml) and the solid was collected and dried in vacuo at 60° C. to give the maleate as a colorless solid (109 mg, 94%), m.p. 201°–203° C.

Elementary analysis for C₂₅H₂₇N₃O₄S.C₄H₄O₄.0.5H₂O: Calculated; C 58.97; H 5.46; N 7.11%. Found; C 59.09; H 5.29; N 6.99%.

EXAMPLE 29

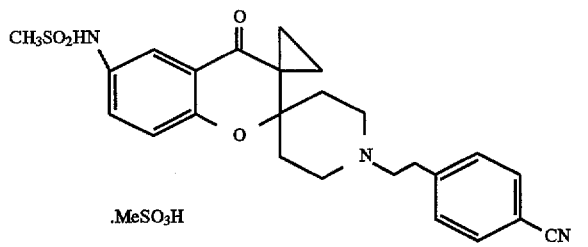

1"-[2-(4-Cyanophenyl)ethyl]-6'-methanesulfonamidodispiro[cyclopropane-1,3'(4'H)-[2H-1]benzopyran-2',4"-piperidine]-4'-one methanesulfonate 1"-[2-(4-Cyanophenyl)ethyl]-6'-methanesulfonamidodispiro-[cyclopropane-1,3'(4'H)-[2H-1]benzopyran-2',4"-piperidine]-4'-one (93 mg, 0.2 mmol) was suspended in ethanol (5 ml) and methanesulfonic acid (13.0 μl, 19.2 mg, 0.2 ml) was added. The mixture was stirred at ambient temperature for 1 h., then the solvent was evaporated under reduced pressure. The residue was recrystallized from EtOH/H$_2$O (10:1, 5 ml) and the solid was collected and dried in vacuo at 60° C. to give the methanesulfonate as a colorless solid (108 mg, 96%), m.p. 285°–287° C.

Elementary analysis for C$_{25}$H$_{27}$N$_3$O$_4$S.CH$_4$O$_3$S.0.65EtOH.0.55H$_2$O: Calculated; C 54.51; H 6.03; N 6.99%. Found; C 54.51; H 6.04; N 6.97%.

EXAMPLE 30

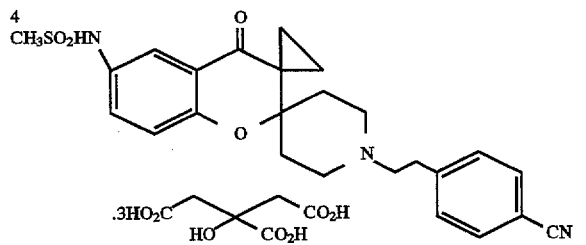

Tetra{1"-[2-(4-cyanophenyl)ethyl]-6'-methanesulfonamidodispiro[cyclopropane-1,3'(4'H)-[2H-1]benzopyran-2',4"-piperidine]-4'-one}tricitrate 1"-[2-(4-Cyanophenyl)ethyl]-6'-methanesulfonamidodispiro-[cyclopropane-1,3'(4'H)-[2H-1]benzopyran-2',4"-piperidine]-4'-one (93 mg, 0.2 mmol) was suspended in ethanol (5 ml) and citric acid (38.4 mg, 0.2 ml) was added. The mixture was stirred at ambient temperature for 1 h., water (0.5 ml) was added and the mixture was heated to reflux. The mixture was filtered, allowed to cool to room temperature and refrigerated. The solid was collected and dried in vacuo at 60° C. to give tetra{1"-[2-(4-cyanophenyl)ethyl]-6'-methanesulfonamidodispiro[-cyclopropane-1,3'(4'H)-[2H-1]benzopyran-2',4"-piperidine]-4'-one}tricitrate as a colorless solid (46 mg, 38%), m.p. 104°–106° C.

Elementary analysis for 4C$_{25}$H$_{27}$N$_3$O$_4$S.3C$_6$H$_8$O$_7$: Calculated; C 58.11; H 5.46; N 6.89%. Found; C 58.08; H 5.58; N 7.08%.

EXAMPLE 31

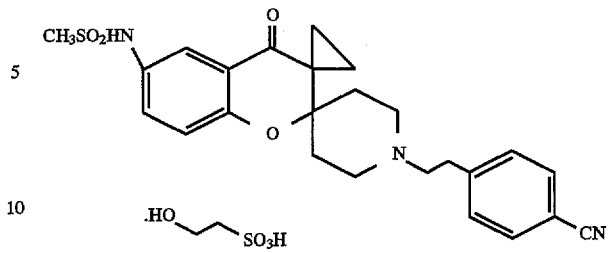

1"-[2-(4-Cyanophenyl)ethyl]-6'-methanesulfonamidodispiro[cyclopropane-1,3'(4'H)-[2H-1]benzopyran-2',4"-piperidine]-4'-one isethionate 1"-[2-(4-Cyanophenyl)ethyl]-6'-methanesulfonamidodispiro-[cyclopropane-1,3'(4'H)-[2H-1]benzopyran-2',4"-piperidine]-4'-one (93 mg, 0.2 mmol) was suspended in ethanol (5 ml) and an aqueous solution of isethionic acid (0.19M, 1.05 ml, 0.2 ml) was added. The mixture was stirred at ambient temperature for 1 h., then the solvent was evaporated under reduced pressure. The residue was recrystallized from EtOH/H$_2$O (10:1, 5 ml) and the solid was collected and dried in vacuo at 60° C. to give the isethionate as a colorless solid (105 mg, 89%), m.p. 264°–266° C.

Elementary analysis for C$_{25}$H$_{27}$N$_3$O$_4$S.C$_2$H$_6$O$_4$S.0.3H$_2$O: Calculated; C 54.31; H 5.67; N 7.04%. Found; C 54.30; H 5.55; N 7.28%.

EXAMPLE 32

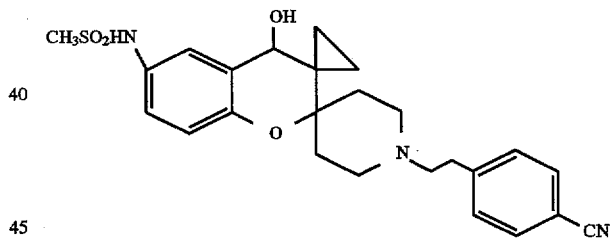

(4'RS)-1"-[2-(4-Cyanophenyl)ethyl]-6'-methanesulfonamidodispiro[cyclopropane-1,3'(4'H)-[2H-1]benzopyran-2',4"-piperidine]-4'-ol Lithium borohydride (26 mg, 1.2 mmol) was added to a stirred suspension of 1"-[2-(4-cyanophenyl)ethyl]-6'-methanesulfonamido-dispiro[cyclopropane-1,3'(4'H)-[2H-1]benzopyran-2',4"-piperidine]-4'-one (140 mg, 0.3 mmol) in THF (10 ml). The yellow solution was stirred at room temperature for 18 h., methanol (1 ml) was added and the solvent was evaporated under reduced pressure. Saturated aqueous sodium hydrogen carbonate (20 ml), water (10 ml) and methanol (5 ml) were added and the mixture was extracted with methylene chloride (3×20 ml). The combined organic fractions were dried (Na$_2$SO$_4$) and evaporated under reduced pressure. Methanol (50 ml) was added and the volume was reduced by distillation to 25 ml. Further methanol (25 ml) was added and the volume was reduced by distillation to 25 ml. The solvent was evaporated under reduced pressure and the residue was purified by flash column chromatography on silica gel, eluting with CH$_2$Cl$_2$/MeOH/NH$_3$ (Aq.) (94:6:0.6 increasing to 90:10:1) to give a colorless foam (136 mg, 97%) which was crystallized from ethanol (3 ml). The solid was collected and dried in vacuo at 60° C. to give the alcohol as a colorless solid (77 mg), m.p. 180°–182° C.

Elementary analysis for C$_{25}$H$_{29}$N$_3$O$_4$S.EtOH: Calculated; C 63.13; H 6.87; N 8.18%. Found; C 62.82; H 6.80; N 8.27%.

EXAMPLE 33

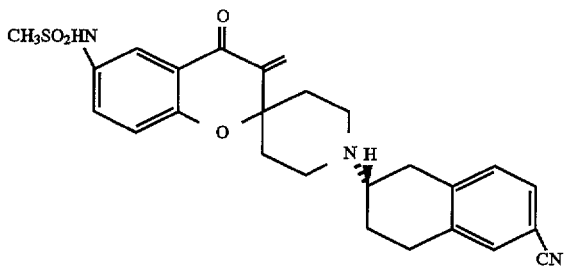

(–)-(2"S)-1'-[(6-Cyano-1,2,3,4-tetrahydronaphthalene)-2-yl]-3,4-dihydro-6-methanesulfonamido-3-methylenespiro(2H-1-benzopyran-2,4'-piperidine)-4-one N,N,N',N'-Tetramethyldiaminomethane (0.316 ml, 0.236 g, 2.31 mmol) was added to a solution of (–)-(2"S)-1'-[(6-cyano-1,2,3,4-tetrahydronaphthalene)-2-yl]-3,4-dihydro-6-methanesulfonamidospiro(2H-1-benzopyran-2,4'-piperidine)-4-one (0.538 g, 1.16 mmol) and acetic acid (0.265 ml, 0.278 g, 4.63 mmol) in THF (10 ml) and the mixture was heated under reflux for 17 h. Further N,N,N',N'-tetramethyldiamino-methane (0.316 ml, 0.236 g, 2.31 mmol) and acetic acid (0.265 ml, 0.278 g, 4.63 mmol) were added and the mixture was heated under reflux for 7 h, cooled and poured into saturated aqueous sodium hydrogen carbonate (50 ml), diluted with water (20 ml) and extracted with methylene chloride (3×50 ml). The combined organic fractions were dried (Na$_2$SO$_4$) and evaporated under reduced pressure. Toluene (150 ml) was added and the volume was reduced by distillation to 75 ml. Further toluene (75 ml) was added and the volume was reduced by distillation to 75 ml. The mixture was allowed to cool with stirring to room temperature then refrigerated overnight. The solid was collected and dried in vacuo to give the ketone as a yellow solid (488 mg, 88%).

δ$_H$(CDCl$_3$) 7.76 (1H, d, J 2.8 Hz), 7.58 (1H, dd, J 8.8, 2.8 Hz), 7.39 (2H, m), 7.19 (1H, d, J 8.3 Hz), 7.06 (1H, d, J 8.8 Hz), 6.6 (1H, br s), 6.41 (1H, s), 5.68 (1H, s), 3.15–2.70 (9H, m), 3.02 (3H, s), and 2.25–1.30 (6H, m).

EXAMPLE 34

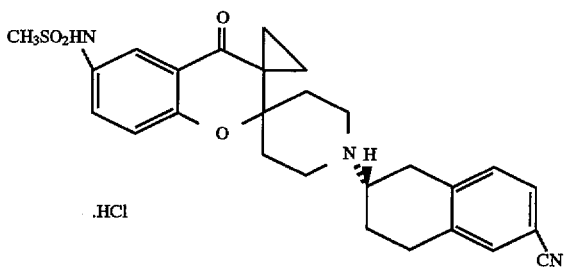

(–)-(2'''S)-1''-[(6-Cyano-1,2,3,4-tetrahydronaphthalene)-2-yl]-6'-methanesulfonamidodispiro[cyclopropane-1,3'(4'H)-[2H-1]benzopyran-2',4''-piperidine]-4'-one hydrochloride Sodium hydride (60% dispersion in mineral oil, 67 mg, 1.7 mmol) was added with water bath cooling to a solution of trimethylsulfoxonium iodide (308 mg, 1.4 mmol) in DMSO (20 ml). The mixture was stirred at room temperature for 20 min. and (–)-(2"S)-1'-[(6-cyano-1,2,3,4-tetrahydronaphthalene)-2-yl]-3,4-dihydro-6-methanesulfonamido-3-methylenespiro(2H-1-benzopyran-2,4'-piperidine)-4-one (334 mg, 0.4 mmol) was added. The mixture was stirred at room temperature for 1 h., poured into saturated aqueous sodium hydrogen carbonate (150 ml), diluted with water (50 ml) and extracted with ethyl acetate (3×150 ml). The combined organic fractions were washed with saturated aqueous sodium hydrogen carbonate (4×150 ml), dried (Na$_2$SO$_4$) and evaporated under reduced pressure. The residue was purified by flash column chromatography on silica gel, eluting with CH$_2$Cl$_2$/MeOH/NH$_3$ (Aq.) (99:1:0.1 increasing to 96:4:0.4) to give a colorless solid (265 mg, 77%). The residue was suspended in ethanol (10 ml) and HCl-EtOH (6M, 1 ml) was added dropwise with stirring. The mixture was stirred at ambient temperature for 1 h., then refrigerated over night. The solid was collected and recrystallized from ethanol/water (10:1, 25 ml). The solid was collected and dried in vacuo at 60° C. to give the hydrochloride as a colorless solid (275 mg), m.p. 250°–252° C., [α]$_d$ –37.8° (c=0.143, MeOH).

Elementary analysis for C$_{27}$H$_{29}$N$_3$O$_4$S.HCl: Calculated; C 61.41; H 5.73; N 7.96%. Found; C 61.18; H 5.78; N 7.90%.

EXAMPLE 35

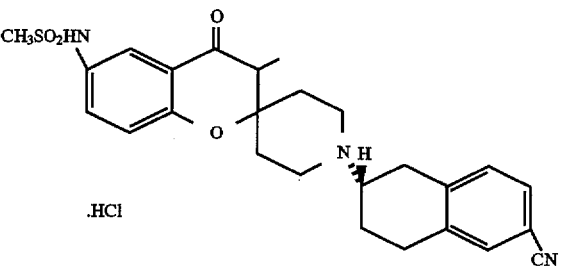

(–)-(3RS,2"S)-1'-[(6-Cyano-1,2,3,4-tetrahydronaphthalene)-2-yl]-3,4-dihydro-6-methanesulfonamido-3-methylspiro(2H-1-benzopyran-2,4'-piperidine)-4-one hydrochloride Palladium on carbon (5%, 15 mg) was added to a suspension of (–)-(2"S)-1'-[(6-cyano-1,2,3,4- tetrahydronaphthalene)-2-yl]-3,4-dihydro-6-methanesulfonamido-3-methylenespiro(2H-1-benzopyran-2,4'-piperidine)-4-one (150 mg, 0.31 mmol) in THF (10 ml) and the mixture was stirred under hydrogen (1 Atm.) for 18 h. Further palladium on carbon (5%, 15 mg) was added and the mixture was stirred under hydrogen (1 Atm.) for 24 h. The mixture was filtered through celite, washing with methanol (50 ml) and the solvent was evaporated under reduced pressure. Saturated aqueous sodium hydrogen carbonate (20 ml) and water (5 ml) were added and the mixture was extracted with methylene chloride (3×20 ml). The combined organic fractions were dried ($Na_2SO_4$) and evaporated under reduced pressure. The residue was purified by flash column chromatography on silica gel, eluting with EtOAc then EtOAc/4% MeOH. The residue was purified by flash column chromatography on silica gel, eluting with $CH_2Cl_2$/MeOH/$NH_3$ (Aq.) (98:2:0.2 increasing to 96:4:0.4) to give a pale yellow foam (129 mg, 83%). The solid was suspended in ethanol (5 ml) and HCl-EtOH (6M, 0.5 ml) was added dropwise with stirring. The mixture was stirred at ambient temperature for 1 h., then the solvent was evaporated under reduced pressure and the residue was recrystallized from ethanol/water (10:1, 10 ml). The solid was collected and dried in vacuo at 60° C. to give the hydrochloride as a colorless solid (53 mg), m.p. 279°–281° C., $[\alpha]_d$ −39.5° (c=0.119, MeOH).

Elementary analysis for $C_{26}H_{29}N_3O_4S\cdot HCl\cdot 0.5EtOH$: Calculated; C 60.15; H 6.17; N 7.80%. Found; C 60.15; H 5.94; N 8.03%.

EXAMPLE 36

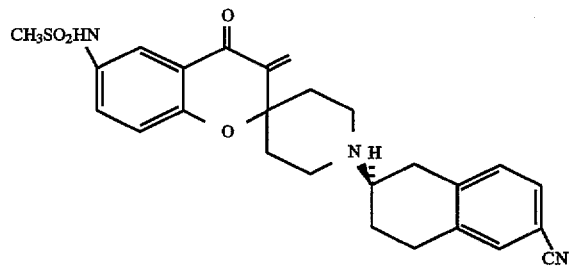

(+)-(2"R)-1'-[(6-Cyano-1,2,3,4-tetrahydronaphthalene)-2-yl]-3,4-dihydro-6-methanesulfonamido-3-methylenespiro(2H-1-benzopyran- 2,4'-piperidine)-4-one N,N,N',N'-Tetramethyldiaminomethane (0.395 ml, 0.296 g, 2.90 mmol) was added to a solution of (+)-(2"R)-1'-[(6-cyano-1,2,3,4-tetrahydronaphthalene)-2-yl]-3,4-dihydro-6-methanesulfonamidospiro(2H-1-benzopyran-2,4'-piperidine)-4-one (0.674 g, 1.45 mmol) and acetic acid (0.332 ml, 0.348 g, 5.80 mmol) in THF (12 ml) and the mixture was heated under reflux for 24 h. Further N,N,N',N'-tetramethyldiamino-methane (0.395 ml, 0.296 g, 2.90 mmol) and acetic acid (0.332 ml, 0.348 g, 5.80 mmol) were added and the mixture was heated under reflux for 6 h, cooled and poured into saturated aqueous sodium hydrogen carbonate (50 ml), diluted with water (20 ml) and extracted with methylene chloride (3×50 ml). The combined organic fractions were dried ($Na_2SO_4$) and evaporated under reduced pressure. Toluene (150 ml) was added and the volume was reduced by distillation to 75 ml. Further toluene (75 ml) was added and the volume was reduced by distillation to 75 ml. The mixture was allowed to cool with stirring to room temperature then refrigerated overnight. The solid was collected and dried in vacuo to give the ketone as a yellow solid (656 mg, 95%).

$\delta_H(CDCl_3)$ 7.76 (1H, d, J 2.8 Hz), 7.58 (1H, dd, J 8.8, 2.8 Hz), 7.39 (2H, m), 7.19 (1H, d, J 8.3 Hz), 7.06 (1H, d, J 8.8 Hz), 6.6 (1H, br s), 6.41 (1H, s), 5.68 (1H, s), 3.15–2.70 (9H, m), 3.02 (3H, s), and 2.25–1.30 (6H, m).

EXAMPLE 37

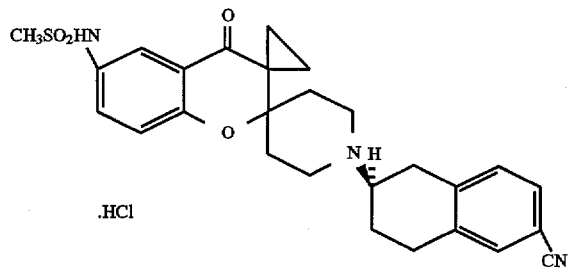

(+)-(2'''R)-1"-[(6-Cyano-1,2,3,4-tetrahydronaphthalene)-2-yl]-6'-methanesulfonamidodispiro[cyclopropane-1,3'(4'H)-[2H-1]benzopyran-2',4"-piperidine]-4'-one hydrochloride Sodium hydride (60% dispersion in mineral oil, 96 mg, 2.4 mmol) was added with water bath cooling to a solution of trimethylsulfoxonium iodide (440 mg, 2.0 mmol) in DMSO (30 ml). The mixture was stirred at room temperature for 20 min. and (+)-(2"R)-1'-[(6-cyano-1,2,3,4-tetrahydronaphthalene)-2-yl]-3,4-dihydro-6-methanesulfonamido-3-methylenespiro(2H-1-benzopyran-2,4'-piperidine)-4-one (477 mg, 1.0 mmol) was added. The mixture was stirred at room temperature for 1 h., poured into saturated aqueous sodium hydrogen carbonate (200 ml), diluted with water (50 ml) and extracted with ethyl acetate (3×200 ml). The combined organic fractions were washed with saturated aqueous sodium hydrogen carbonate (4×200 ml), dried ($Na_2SO_4$) and evaporated under reduced pressure. The residue was purified by flash column chromatography on silica gel, eluting with $CH_2Cl_2$/MeOH/$NH_3$ (Aq.) (99:1:0.1 increasing to 96:4:0.4) to give a colorless solid (429 mg, 87%). A sample (250 mg) was suspended in ethanol (10 ml) and HCl-EtOH (6M, 1 ml) was added dropwise with stirring. The mixture was stirred at ambient temperature for 1 h. then refrigerated over night. The solid was collected and recrystallized from ethanol/water (10:1, 25 ml). The solid was collected and dried in vacuo at 60° C. to give the hydrochloride as a colorless solid (226 mg), m.p. 250°–252° C., $[\alpha]_d$ +38.6° (c=0.119, MeOH).

Elementary analysis for $C_{27}H_{29}N_3O_4S\cdot HCl$: Calculated; C 61.41; H 5.73; N 7.96%. Found; C 61.32; H 5.81; N 7.80%.

EXAMPLE 38

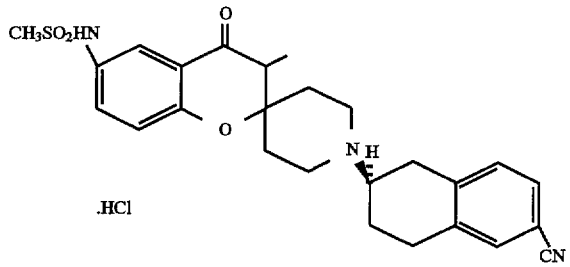

(+)-(3RS,2"R)-1'-[(6-Cyano-1,2,3,4-
tetrahydronaphthalene)-2-yl]-3,4-dihydro-6-
methanesulfonamido-3-methylspiro(2H-1-
benzopyran-2,4'-piperidine)-4-one hydrochloride Palladium on carbon (5%, 17 mg) was added to a suspension of (+)-(2"R)-1'-[(6-cyano-1,2,3,4-tetrahydronaphthalene)-2-yl]-3,4-dihydro-6-methanesulfonamido-3-methylenespiro(2H-1-benzopyran-2,4'-piperidine)-4-one (170 mg, 0.36 mmol) in THF (10 ml) and the mixture was stirred under hydrogen (1 Atm.) for 6 h. Further palladium on carbon (5%, 17 mg) was added and the mixture was stirred under hydrogen (1 Atm.) for 18 h. The mixture was filtered through celite, washing with methanol (50 ml) and the solvent was evaporated under reduced pressure. Saturated aqueous sodium hydrogen carbonate (20 ml) and water (5 ml) were added and the mixture was extracted with methylene chloride (3×20 ml). The combined organic fractions were dried ($Na_2SO_4$) and evaporated under reduced pressure. The residue was purified by flash column chromatography on silica gel, eluting with EtOAc/MeOH/$NH_3$ (Aq.) (99:1:0.1 increasing to 97:3:0.3) to give an off-white solid (140 mg, 85%). The solid was suspended in ethanol (5 ml) and HCl-EtOH (6M, 0.5 ml) was added dropwise with stirring. The mixture was stirred at ambient temperature for 1 h., then the solvent was evaporated under reduced pressure and the residue was recrystallized from ethanol/water (10:1, 10 ml). The solid was collected and dried in vacuo at 60° C. to give the hydrochloride as a colorless solid (67 mg), m.p. 279°–281° C., $[\alpha]_d$ +40.3° (c=0.142, MeOH).

Elementary analysis for $C_{26}H_{29}N_3O_4S.HCl.0.5EtOH$: Calculated; C 60.15; H 6.17; N 7.80%. Found; C 59.91; H 5.88; N 7.75%.

EXAMPLE 39

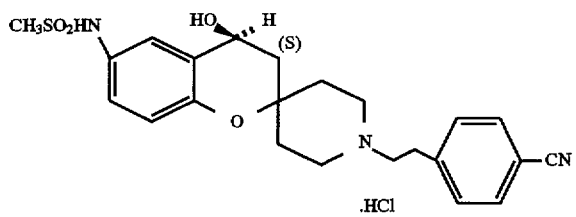

(+)-(4S)-1'-[2-(4-Cyanophenyl)ethyl]-3,4-dihydro-6-
methanesulfonamido-spiro(2H-1-benzopyran-2,4'-
piperidine)-4-ol hydrochloride 1'-[2-(4-Cyanophenyl)ethyl]-3,4-dihydro-6-methanesulfonamidospiro(2H-1-benzopyran-2,4'-piperidine)-4-one (600 mg, 1.37 mmol) was dissolved in methylene chloride (20 ml) and cooled to –20° C. A solution of (R)-tetrahydro-1-methyl-3,3-diphenyl-1H,3H-pyrrolo[1,2,c]-[1,3,2]oxazaborole-borane complex (692 mg, 2.39 mmol) in methylene chloride (10 ml) was added dropwise (Reaction temperature<–15° C.) and the mixture was stirred under argon at –15° C. for 1 h, then at ambient temperature for 1 h. The solvent was evaporated under reduced pressure and the residue was purified by flash column chromatography on silica gel, eluting with $CH_2Cl_2$/MeOH/$NH_3$ (Aq.) (99:1:0.1) to give a colorless foam. The residue was dissolved in methylene chloride (10 ml) and cooled to 0° C. Acetic anhydride (150 µl, 162 mg, 1.6 mmol) was added dropwise and the mixture was stirred at 0° C. for 1 h. Methanol (5 ml) was added and the mixture was stirred at room temperature for 18 h. Saturated aqueous sodium hydrogen carbonate (10 ml) and water (10 ml) were added, the layers were separated and the aqueous layer was extracted with methylene chloride (2×20 ml). The combined organic fractions were dried ($Na_2SO_4$) and evaporated under reduced pressure. The residue was purified by flash column chromatography on silica gel, eluting with $CH_2Cl_2$/MeOH/ $NH_3$ (Aq.) (95:5:0.5 increasing to 93:7:0.7) to give a colorless foam (548 mg, 91%). A sample was dissolved in ethanol (5 ml) and HCl-EtOH (6M, 0.5 ml) was added dropwise with stirring. The mixture was stirred at ambient temperature for 1 h., then refrigerated over night. The solid was collected and dried in vacuo at 60° C. to give the hydrochloride as a colorless solid, m.p. 166°–170° C., $[\alpha]_d$ +13.3° (c=0.030, MeOH).

Elementary analysis for $C_{23}H_{27}N_3O_4S.HCl.0.3H_2O.0.65EtOH$: Calculated; C 56.85; H 6.38; N 8.19%. Found; C 56.85; H 6.05; N 8.12%.

EXAMPLE 40

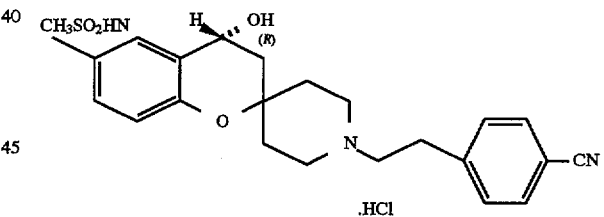

(–)-(4R)-1'-[2-(4-Cyanophenyl)ethyl]-3,4-dihydro-6-
methanesulfonamidospiro(2H-1-benzopyran-2,4'-
piperidine)-4-ol hydrochloride 1'-[2-(4-Cyanophenyl)ethyl]-3,4-dihydro-6-methanesulfonamidospiro(2H-1-benzopyran-2,4'-piperidine)-4-one (601 mg, 1.37 mmol) was dissolved in methylene chloride (20 ml) and cooled to –20° C. A solution of (S)-tetrahydro-1-methyl-3,3-diphenyl-1H,3H-pyrrolo[1,2,c]-[1,3,2]oxazaborole-borane complex (691 mg, 2.39 mmol) in methylene chloride (5 ml) was added dropwise (Reaction temperature<–15° C.) and the mixture was stirred under argon at –15° C. for 1 h, then at ambient temperature for 1 h. The solvent was evaporated under reduced pressure. Methanol (50 ml) was added and the volume was reduced by distillation to 25 ml. Further methanol (30 ml) was added, the volume was reduced by distillation to 25 ml and the solvent was evaporated under reduced pressure. The residue was dissolved in methylene chloride (10 ml) and cooled to 0° C. Acetic anhydride (150 μl, 162 mg, 1.6 mmol) was added dropwise and the mixture was stirred at 0° C. for 1 h, then at room temperature for 1 h. Methanol (5 ml) was added and the mixture was stirred at room temperature for 18 h. Saturated aqueous sodium hydrogen carbonate (10 ml) and water (10 ml) were added, the layers were separated and the aqueous layer was extracted with methylene chloride (2×30 ml). The combined organic fractions were dried ($Na_2SO_4$) and evaporated under reduced pressure. The residue was purified by flash column chromatography on silica gel, eluting with $CH_2Cl_2$/MeOH/$NH_3$ (Aq.) (95:5:0.5 increasing to 93:7:0.7). The residue was purified by flash column chromatography on silica gel, eluting with EtOAc/MeOH/$NH_3$ (Aq.) (96:4:0.4 increasing to 90:10:1) to give a colorless foam (371 mg, 61%). The residue was dissolved in ethanol (5 ml) and HCl-EtOH (6M, 0.5 ml) was added dropwise with stirring. Ether was added and the solid was collected and dried in vacuo at 60° C. to give the hydrochloride as a colorless solid, m.p. 158°–160° C., $[\alpha]_d$ –12.5° (c=0.032, MeOH).

Elementary analysis for $C_{23}H_{27}N_3O_4S \cdot HCl \cdot 0.55H_2O \cdot 0.05EtOH$: Calculated; C 56.59; H 6.05; N 8.57%. Found; C 56.60; H 5.97; N 8.51%.

EXAMPLE 41

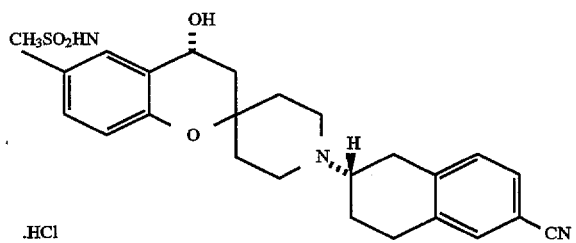

(–)-(4R, 2"S)-1'-[(6-Cyano-1,2,3,4-tetrahydronaphthalene)-2-yl]-3,4-dihydro-6-methanesulfonamidospiro(2H-1-benzopyran-2,4'-piperidine)-4-ol hydrochloride (–)-(2"S)-1'-[(6-Cyano-1,2,3,4-tetrahydronaphthalene)-2-yl]-3,4-dihydro-6-methanesulfonamidospiro(2H-1-benzopyran-2,4'-piperidine)-4-one (465 mg, 1.0 mmol) was dissolved in methylene chloride (20 ml) and cooled to –20° C. A solution of (S)-tetrahydro-1-methyl-3,3-diphenyl-1H,3H-pyrrolo[1,2,c][1,3,2]oxazaborole-borane complex (349 mg, 1.2 mmol) in methylene chloride (5 ml) was added dropwise (Reaction temperature <–15° C.) and the mixture was stirred under argon at –15° C. for 1 h, then at ambient temperature for 1 h. Methanol (1 ml) was added and the solvent was evaporated under reduced pressure. Methanol (30 ml) was added and the volume was reduced by distillation to 10 ml. Further methanol (30 ml) was added, the volume was reduced by distillation to 10 ml and the solvent was evaporated under reduced pressure. The residue was dissolved in methylene chloride (20 ml) and cooled to 0° C. Acetic anhydride (119 μl, 128 mg, 1.26 mmol) was added dropwise and the mixture was stirred at 0° C. for 1 h. Further acetic anhydride (11 μl, 12 mg, 0.12 mmol) was added and the mixture was stirred at 0° C. for 1 h. Methanol (5 ml) was added and the mixture was stirred at room temperature for 17 h. Saturated aqueous sodium hydrogen carbonate (10 ml) and water (5 ml) were added, the layers were separated and the aqueous layer was extracted with methylene chloride (2×20 ml). The combined organic fractions were dried ($Na_2SO_4$) and evaporated under reduced pressure. The residue was purified by flash column chromatography on silica gel, eluting with $CH_2Cl_2$/MeOH/$NH_3$ (Aq.) (93:7:0.7) to give (–)-(4R,2"S)-1'-[(6-cyano-1,2,3,4-tetrahydronaphthalene)-2-yl]-3,4-dihydro-6-methanesulfonamidospiro(2H-1-benzopyran-2,4'-piperidine)-4-ol as a colorless foam containing 8% methylene chloride by $^1$H NMR (460 mg, 91%). A sample (454 mg) was dissolved in ethanol (5 ml) and HCl-EtOH (6M, 0.5 ml) was added dropwise with stirring. The mixture was stirred at ambient temperature for 1 h., then refrigerated over night. The solid was collected and dried in vacuo at 35° C. to give the hydrochloride as a colorless solid (306 mg), m.p. 191°–193° C., $[\alpha]_d$ –53.2° (c=0.176, MeOH).

Elementary analysis for $C_{25}H_{29}N_3O_4S \cdot HCl \cdot 1.3H_2O$: Calculated; C 56.92; H 6.23; N 7.97%. Found; C 56.92; H 6.05; N 7.93%.

EXAMPLE 42

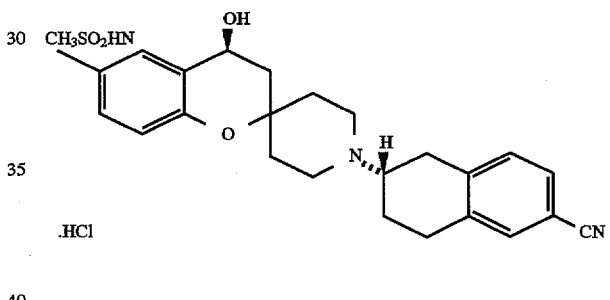

(–)-(4S,2"S)-1'-[(6-Cyano-1,2,3,4-tetrahydronaphthalene)-2-yl]-3,4-dihydro-6-methanesulfonamidospiro(2H-1-benzopyran-2,4'-piperidine)-4-ol hydrochloride (–)-(2"S)-1'-[(6-Cyano-1,2,3,4-tetrahydronaphthalene)-2-yl]-3,4-dihydro-6-methanesulfonamidospiro(2H-1-benzopyran-2,4'-piperidine)-4-one (465 mg, 1.0 mmol) was dissolved in methylene chloride (20 ml) and cooled to –20° C. A solution of (R)-tetrahydro-1-methyl-3,3-diphenyl-1H,3H-pyrrolo[1,2,c][1,3,2]oxazaborole-borane complex (349 mg, 1.2 mmol) in methylene chloride (5 ml) was added dropwise (Reaction temperature <–15° C.) and the mixture was stirred under argon at –15° C. for 1 h, then at ambient temperature for 1 h. Methanol (1 ml) was added and the solvent was evaporated under reduced pressure. Methanol (30 ml) was added and the volume was reduced by distillation to 10 ml. Further methanol (30 ml) was added, the volume was reduced by distillation to 10 ml and the solvent was evaporated under reduced pressure. The residue was dissolved in methylene chloride (20 ml) and cooled to 0° C. Acetic anhydride (119 μl, 128 mg, 1.26 mmol) was added dropwise and the mixture was stirred at 0° C. for 1 h. Further acetic anhydride (11 μl, 12 mg, 0.12 mmol) was added and the mixture was stirred at 0° C. for 1 h. Methanol (5 ml) was added and the mixture was stirred at room temperature for 17 h. Saturated aqueous sodium hydrogen carbonate (10 ml) and water (5 ml) were added, the layers were separated and the aqueous layer was extracted with methylene chloride (2×20 ml). The combined organic fractions were dried (Na$_2$SO$_4$) and evaporated under reduced pressure. The residue was purified by flash column chromatography on silica gel, eluting with CH$_2$Cl$_2$/MeOH/NH$_3$ (Aq.) (93:7:0.7) to give (−)-(4S,2"S)-1'-[(6-Cyano-1,2,3,4-tetrahydronaphthalene)-2-yl]-3,4-dihydro-6-methanesulfonamidospiro(2H-1-benzopyran-2,4'-piperidine)-4-ol as a colorless foam containing 15% methylene chloride by $^1$H NMR (510 mg, 93%). A sample (500 mg) was dissolved in ethanol (5 ml) and HCl-EtOH (6M, 0.5 ml) was added dropwise with stirring. The mixture was stirred at ambient temperature for 1 h., then refrigerated over night. The solid was collected and dried in vacuo at 35° C. to give the hydrochloride as a colorless solid (409 mg), m.p. 210°–212° C., [α]$_d$ −26.2° (c=0.176, MeOH).

Elementary analysis for C$_{25}$H$_{29}$N$_3$O$_4$S.HCl.0.6H$_2$O: Calculated; C 58.32; H 6.11; N 8.16%. Found; C 58.27; H 5.82; N 8.15%.

EXAMPLE 43

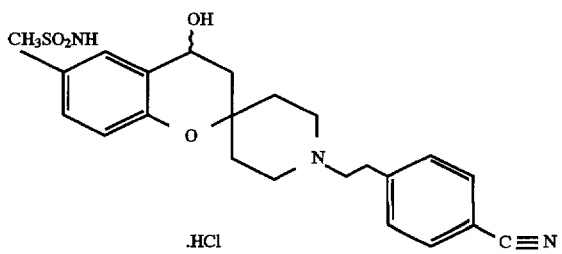

(4RS)-1'-[2-(4-Cyanophenyl)ethyl]-3,4-dihydro-6-methanesulfonamidospiro(2H-1-benzopyran-2,4'-piperidine)-4-ol hydrochloride Sodium borohydride (30 mg, 0.80 mmol) was added to a stirred, cooled (0° C.) suspension of 1'-[2-(4-cyanophenyl)ethyl]-3,4-dihydro-6-methanesulfonamidospiro(2H-1-benzopyran-2,4'-piperidine)-4-one hydrochloride (190 mg, 0.40 mmol) in ethanol (4 ml). The mixture was stirred at 0° C. for 3 h., further sodium borohydride (30 mg, 0.80 mmol) was added and the mixture was stirred at room temperature for 18 h. Water (3 ml) and saturated aqueous sodium hydrogen carbonate (2 ml) were added and the ethanol was evaporated under reduced pressure. The mixture was extracted with methylene chloride (3×5 ml) and the combined organic fractions were washed with brine, dried (Na$_2$SO$_4$) and evaporated under reduced pressure. The residue was purified by flash column chromatography on silica gel, eluting with EtOAc/MeOH (90:10) to give a colorless foam (136 mg, 77%). The residue was dissolved in ethanol (3 ml), cooled to 0° C. and HCl-EtOH (6.9M, 55 μl) was added dropwise with stirring. The mixture was stirred at ambient temperature for 1 h. then refrigerated overnight. The solid was collected and dried in vacuo at 60° C. to give the hydrochloride as a colorless solid (130 mg), m.p. 245°–246° C.

Elementary analysis for C$_{23}$H$_{27}$N$_3$O$_4$S.HCl.0.15EtOH: Calculated; C 57.71; H 6.01; N 8.67%. Found; C 57.57; H 5.95; N 8.37%.

EXAMPLE 44

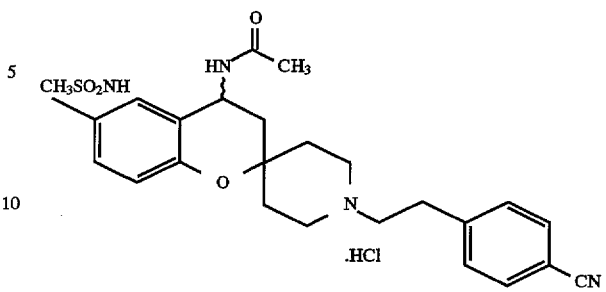

(4RS)-4-Acetamido-1'-[2-(4-cyanophenyl)ethyl]-3,4-dihydro-6-methane-sulfonamidospiro(2H-1-benzopyran-2,4'-piperidine)hydrochloride A solution of (4RS)-1'-[2-(4-cyanophenyl)ethyl]-3,4-dihydro-6-methanesulfonamidospiro(2H-1-benzopyran-2,4'-piperidine)-4-ol (500 mg, 1.1 mmol) in acetonitrile at room temperature was treated with concentrated sulfuric acid (0.40 ml) and the reaction stirred at room temperature for 2 h. The reaction was poured into saturated aqueous sodium bicarbonate (250 ml) and extracted with ethyl acetate (3×200 ml). The combined extracts were dried over anhydrous magnesium sulfate, filtered, and concentrated at reduced pressure. The residue was chromatographed on silica gel with chloroform/methanol (97:3 to 90:10) as eluent to give 0.404 g of free base. This material was treated with excess ethanolic HCl and the product crystallized from ethanol to give the hydrochloride (327 mg, 57%), m.p.>275° C.

Elementary analysis for C$_{25}$H$_{30}$N$_4$O$_4$S.HCl.0.3EtOH.0.2H$_2$O: Calculated; C 57.31; H 6.24; N 10.44%. Found; C 57.33; H 6.21; N 10.20%.

EXAMPLE 45

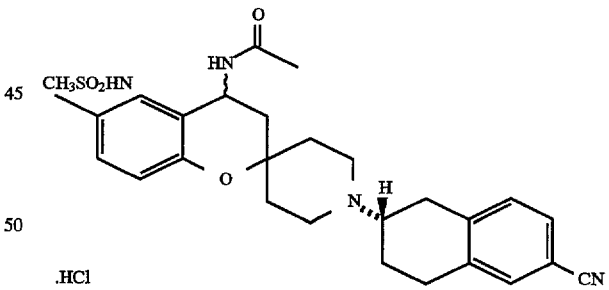

(4RS,2"S)-4-Acetamido-1'-[(6-cyano-1,2,3,4-tetrahydronaphthalene)-2-yl]-3,4-dihydro-6-methanesulfonamidospiro(2H-1-benzopyran-2,4'-piperidine)hydrochloride (−)-(4RS,2"S)-1'-[(6-Cyano-1,2,3,4-tetrahydronaphthalene)-2-yl]-3,4-dihydro-6-methanesulfonamidospiro(2H-1-benzopyran-2,4'-piperidine)-4-ol (200 mg, 0.43 mmol) was dissolved in acetonitrile (5 ml) and cooled to −15° C. Sulfuric acid (98%, 0.128 ml, 230 mg, 2.35 mmol) was added and the mixture was stirred at room temperature for 1 h. The solid precipitate was collected and dissolved in methylene chloride (20 ml).

Saturated aqueous sodium hydrogen carbonate (20 ml) was added, the layers were separated and the aqueous layer was extracted with methylene chloride (2×20 ml). The combined organic fractions were dried ($Na_2SO_4$) and evaporated under reduced pressure to give a colorless oil (0.18 g, 82%). The residue was dissolved in ethanol and HCl-$^i$PrOH (1.3M, 0.4 ml) was added dropwise with stirring. The mixture was stirred at ambient temperature and the solid was collected and dried in vacuo at 95° C. to give the hydrochloride as a colorless solid (0.165 g), m.p.>300° C.

Elementary analysis for $C_{27}H_{32}N_4O_4S.HCl.0.35H_2O$: Calculated; C 58.81; H 6.16; N 10.16%. Found; C 58.81; H 5.90; N 10.01%.

EXAMPLE 46

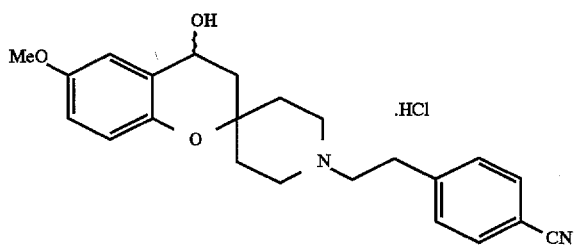

(4RS)-1'-[2-(4-Cyanophenyl)ethyl]-3,4-dihydro-6-methoxyspiro(2H-1-benzopyran-2,4'-piperidine)-4-ol hydrochloride A solution of 1'-[2-(4-cyanophenyl)ethyl]-3,4-dihydro-6-methoxyspiro(2H-1-benzopyran-2,4'-piperidine)-4-one hydrochloride (412 mg, 1 mmol) in ethanol (25 ml) at room temperature was treated with sodium borohydride (0.10 g, 2.65 mmol) and stirred at room temperature for 1 h. The reaction was poured into saturated aqueous sodium bicarbonate and extracted with ethyl acetate. The combined extracts were dried over anhydrous magnesium sulfate, filtered, and concentrated at reduced pressure. The residue was chromatographed on silica gel with chloroform/methanol (95:5) as eluent to give 0.322 g of free base. The material thus obtained was treated with excess ethanolic HCl and the product crystallized from ethanol to give the hydrochloride (215 mg, 52%), m.p. 224°–226° C.

Elementary analysis for $C_{23}H_{26}N_2O_3.HCl.0.1EtOH.0.35H_2O$: Calculated; C 65.43; H 6.70; N 6.58%. Found; C 65.44; H 6.60; N 6.43%.

EXAMPLE 47

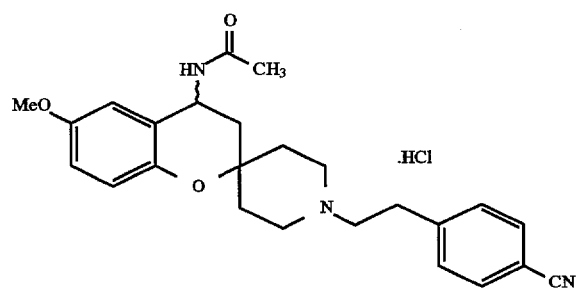

(4RS)-4-Acetamido-1-[2-(4-cyanophenyl)ethyl]-3,4-dihydro-6-methoxy-spiro(2H-1-benzopyran-2,4'-piperidine)hydrochloride A solution of (4RS)-1'-[2-(4-cyanophenyl)ethyl]-3,4-dihydro-6-methoxyspiro(2H-1-benzopyran-2,4'-piperidine)-4-ol (600 mg, 1.6 mmol) in acetonitrile at room temperature was treated with concentrated sulfuric acid (0.25 ml) and the reaction stirred at room temperature for 2 h. The reaction was poured into saturated aqueous sodium bicarbonate (300 ml) and extracted with ethyl acetate (3×100 ml). The combined extracts were dried over anhydrous magnesium sulfate, filtered, and concentrated at reduced pressure. The residue was chromatographed on silica gel with chloroform/methanol (97:3 to 95:5) as eluent to give 0.310 g of free base. This material was treated with excess ethanolic HCl and the product crystallized from ethanol to give the hydrochloride (195 mg, 27%), m.p. 250° C.

Elementary analysis for $C_{25}H_{29}N_3O_3.HCl.0.05EtOH.1.10H_2O$: Calculated; C 63.05; H 6.85; N 8.79%. Found; C 62.72; H 6.46; N 8.77%.

EXAMPLE 48

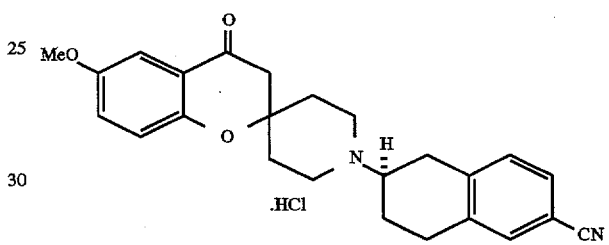

(+)-(2"R)-1'-(6-Cyano-1,2,3,4-tetrahydronaphthalen-2-yl)-3,4-dihydro-6-methoxyspiro(2H-1-benzopyran-2,4'-piperidine)-4-one hydrochloride A solution of 5'-methoxy-2'-hydroxyacetophenone (8.5 g, 51.16 mmol) in methanol (400 ml) al room temperature was treated with pyrrolidine (3.63 g, 51.16 mmol). The reaction was stirred at room temperature for 5 min., (2'R)-N-(6-cyano-1',2',3',4'-tetrahydronapthalen-2-yl)piperidin-4-one (10 g, 39.3 mmol) was added and the reaction stirred at ambient temperature for 18 h. The reaction was concentrated at reduced pressure and the residue was partitioned between ethyl acetate (500 ml) and saturated sodium bicarbonate (500 ml). The layers were separated and the aqueous phase was extracted with two additional 300 ml portions of ethyl acetate. The combined extracts were dried over anhydrous magnesium sulfate, filtered, and concentrated at reduced pressure. The residue was chromatographed on silica gel with chloroform/methanol (98:2 to 90:10) as eluent to give 9.3 g of free base. A 200 mg sample of this material was treated with excess ethanolic HCl and the product crystallized from ethanol to give the hydrochloride (132 mg, 36%), m.p. 270°–272° C., $[\alpha]_d$ +44.6° (c=0.3, MeOH).

Elementary analysis for $C_{25}H_{26}N_2O_3.HCl.H_2O$: Calculated; C 65.70; H 6.40; N 6.41%. Found; C 65.95; H 6.14; N 6.29%.

EXAMPLE 49

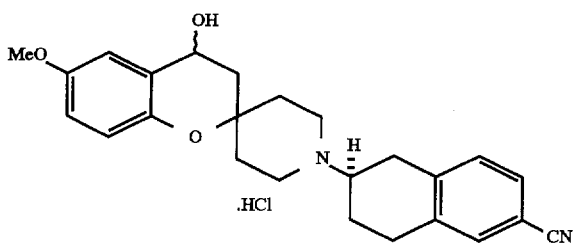

(4RS,2"R)-1'-(6-Cyano-1,2,3,4-tetrahydronaphthalen-2-yl)-3,4-dihydro-6-methoxyspiro(2H-1-benzopyran-2,4'-piperidine)-4-ol hydrochloride A solution of (+)-(2"R)-1'-(6-cyano-1,2,3,4-tetrahydronaphthalen-2-yl)-3,4-dihydro-6-methoxyspiro (2H-1-benzopyran-2,4'-piperidine)-4-one (1.2 g, 3 mmol) in ethanol (100 ml) at room temperature was treated with sodium borohydride (0.22 g, 5.8 mmol) and stirred at room temperature for 1 h. The reaction was poured into saturated aqueous sodium bicarbonate (300 ml) and extracted with ethyl acetate (3×200 ml). The combined extracts were dried over anhydrous magnesium sulfate, filtered, and concentrated at reduced pressure. The residue was chromatographed on silica gel with chloroform/methanol (98:2 to 90:10) as eluent to give 0.98 g of free base. A 180 mg sample of the material thus obtained was treated with excess ethanolic HCl and the product crystallized from ethanol to give the hydrochloride (140 mg, 58%), m.p. 265°–267° C.

Elementary analysis for $C_{25}H_{28}N_2O_3.HCl.0.45EtOH$: Calculated; C 67.37; H 6.92; N 6.07%. Found; C 67.70; H 6.93; N 5.98%.

EXAMPLE 50

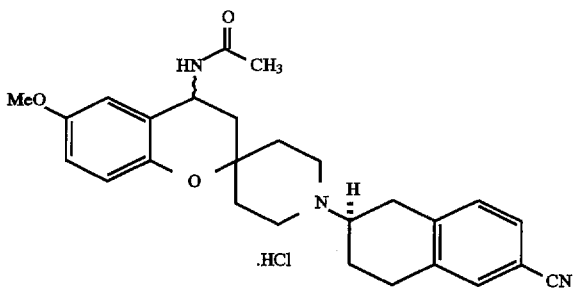

(4RS,2"R)-4-Acetamido-1'-(6-cyano-1,2,3,4-tetrahydronaphthalen-2-yl)-3,4-dihydro-6-methoxyspiro(2H-1-benzopyran-2,4'-piperidine) hydrochloride A solution of (4RS,2"R)-1'-(6-cyano-1,2,3,4-tetrahydronaphthalen-2-yl)-3,4-dihydro-6-methoxyspiro (2H-1-benzopyran-2,4'-piperidine)-4-ol (800 mg, 1.98 mmol) in acetonitrile at room temperature was treated with concentrated sulfuric acid (0.27ml) and the reaction stirred at room temperature for 2 h. The reaction was poured into saturated aqueous sodium bicarbonate (300 ml) and extracted with ethyl acetate (3×200 ml). The combined extracts were dried over anhydrous magnesium sulfate, filtered, and concentrated at reduced pressure. The residue was chromatographed on silica gel with chloroform/methanol (97:3 to 93:7) as eluent to give 0.522 g of free base. This material was treated with excess ethanolic HCl and the product crystallized from ethanol to give the hydrochloride (303 mg, 32%), m.p.>315° C.

Elementary analysis for $C_{27}H_{31}N_3O_3.HCl.0.60H_2O$: Calculated; C 65.80; H 6.79; N 8.53%. Found; C 65.78; H 6.56; N 8.60%.

EXAMPLE 51

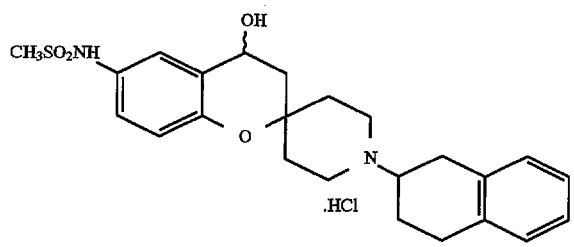

(4RS)-3,4-Dihydro-6-methanesulfonamido-1'-(1,2,3,4-tetrahydronaphthalen-2-yl)spiro(2H-1-benzopyran-2,4'-piperidine)-4-ol hydrochloride A solution of (+)-3,4-dihydro-6-methanesulfonamido-1'-(1,2,3,4-tetrahydronaphthalen-2-yl)spiro(2H-1-benzopyran-2,4'-piperidine)-4-one hydrochloride (103 mg, 0.215 mmol) in ethanol (10 ml) at room temperature was treated with sodium borohydride (0.050 g, 1.3 mmol) and stirred at room temperature for 1 h. The reaction was poured into saturated aqueous sodium bicarbonate and extracted with ethyl acetate. The combined extracts were dried over anhydrous magnesium sulfate, filtered, and concentrated at reduced pressure. The residue was chromatographed on silica gel with chloroform/methanol (95:5) as eluent to give 0.071 g of free base. The material thus obtained was treated with excess ethanolic HCl and the product crystallized from ethanol to give the hydrochloride (32 mg, 31%), m.p.>236° C.

Elementary analysis for $C_{24}H_{30}N_2O_4S.HCl.0.70H_2O$: Calculated; C 58.63; H 6.64; N 5.70%. Found; C 58.60; H 6.37; N 5.57%.

EXAMPLE 52

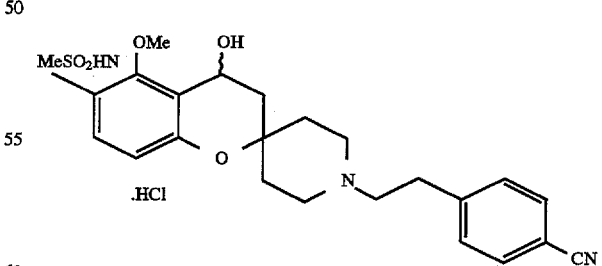

(4RS)-1'-[2-(4-Cyanophenyl)ethyl]-3,4-dihydro-6-methanesulfonamido-5-methoxyspiro(2H-1-benzopyran-2,4'-piperidine)-4-ol hydrochloride Sodium borohydride (13.5 mg, 0.36 mmol) was added to a stirred, cooled (0° C.) suspension of 1'-[2-(4-cyanophenyl)

ethyl]-3,4-dihydro-6-methanesulfonamido-5-methoxyspiro (2H-1-benzopyran-2,4'-piperidine)-4-one hydrochloride (90 mg, 0.18 mmol) in ethanol (1 ml). The mixture was stirred at 0° C. for 3 h., further sodium borohydride (13.5 mg, 0.36 mmol) was added and the mixture was stirred at room temperature for 18 h. The solvent was evaporated under reduced pressure and saturated aqueous sodium hydrogen carbonate (5 ml) was added. The mixture was extracted with ethyl acetate (4×5 ml) and the combined organic fractions were dried (MgSO$_4$) and evaporated under reduced pressure. The residue was purified by flash column chromatography on silica gel, eluting with CH$_2$Cl$_2$/MeOH/NH$_3$ (Aq.) (95:5:0.5) to give a colorless foam (68 mg, 93%). The residue was dissolved in ethanol (2 ml), cooled to 0° C. and HCl-EtOH (6M, 0.5 ml) was added dropwise with stirring. The mixture was stirred at ambient temperature for 1 h. then refrigerated overnight. The solid was collected and dried in vacuo at 50° C. to give the hydrochloride as a colorless solid, m.p. 165°–170° C.

Elementary analysis for C$_{24}$H$_{29}$N$_3$O$_5$S.HCl.1.4H$_2$O.0.7EtOH: Calculated; C 53.94; H 6.60; N 7.43%. Found; C 53.94; H 6.20; N 7.31%.

EXAMPLE 53

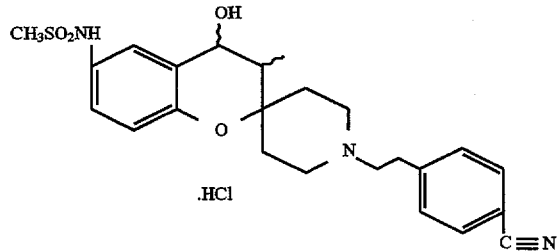

(3RS,4RS)-1'-[2-(4-Cyanophenyl)ethyl]-3,4-dihydro-6-methanesulfonamido-3-methylspiro(2H-1-benzopyran-2,4'-piperidine)-4-ol hydrochloride Sodium borohydride (30 mg, 0.78 mmol) was added to a stirred, cooled (0° C.) suspension of (3RS)-1'-[2-(4-cyanophenyl)ethyl]-3,4-dihydro-6-methanesulfonamido-3-methylspiro(2H-1-benzopyran-2,4'-piperidine)-4-one (177 mg, 0.39 mmol) in ethanol (4 ml). The mixture was stirred at 0° C. for 1 h., further sodium borohydride (15 mg, 0.39 mmol) was added and the mixture was stirred at room temperature for 18 h. Water (2 ml) and saturated aqueous sodium hydrogen carbonate (3 ml) were added and the ethanol was evaporated under reduced pressure. The mixture was extracted with methylene chloride (4×5 ml) and the combined organic fractions were washed with brine, dried (Na$_2$SO$_4$) and evaporated under reduced pressure. The residue was purified by flash column chromatography on silica gel, eluting with EtOAc/MeOH (90:10) to give a colorless foam (139 mg, 78%). The residue was dissolved in ethanol (2 ml), cooled to 0° C. and HCl-EtOH (6.9M, 51 μl) was added dropwise with stirring. The mixture was stirred at ambient temperature for 20 min. then refrigerated overnight. The solid was collected and dried in vacuo at 50° C. to give the hydrochloride as a colorless solid (121 mg) (3:2 mixture of diastereoisomers, determined by HPLC), m.p. 264°–265° C.

Elementary analysis for C$_{24}$H$_{29}$N$_3$O$_4$S.HCl.0.6H$_2$O: Calculated; C 57.32; H 6.25; N 8.36%. Found; C 57.27; H 6.10; N 8.30%.

EXAMPLE 54

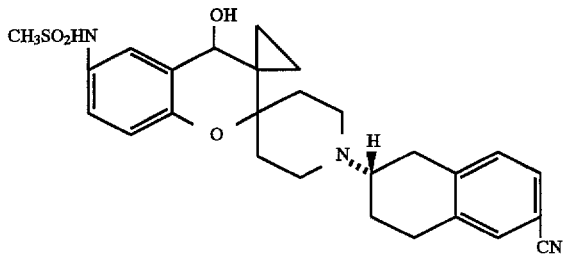

(–)-(4'RS,2'''S)-1''-[(6-Cyano-1,2,3,4-tetrahydronaphthalene)-2-yl]-6'-methanesulfonamidodispiro[cyclopropane-1,3'(4'H)-[2H-1]benzopyran-2',4''-piperidine]-4'-ol Lithium borohydride (20 mg, 0.92 mmol) was added to a stirred suspension of (–)-(2'''S)-1''-[(6-cyano-1,2,3,4-tetrahydronaphthalene)-2-yl]-6'-methanesulfonamidodispiro[cyclopropane-1,3'(4'H)-[2H-1]benzopyran-2',4''-piperidine]-4'-one (113 mg, 0.23 mmol) in THF (10 ml) and the yellow solution was stirred at room temperature for 17 h. Methanol (1 ml) was added and the mixture was poured into saturated aqueous sodium hydrogen carbonate (40 ml) and water (10 ml). The mixture was extracted with methylene chloride (3×40 ml) and the combined organic fractions were dried (Na$_2$SO$_4$) and evaporated under reduced pressure. Methanol (50 ml) was added and the volume was reduced by distillation to 25 ml. Further methanol (25 ml) was added and the volume was reduced by distillation to 25 ml. The solvent was evaporated under reduced pressure and the residue was purified by flash column chromatography on silica gel, eluting with CH$_2$Cl$_2$/MeOH/NH$_3$ (Aq.) (96:4:0.4 increasing to 90:10:1) to give a colorless foam (110 mg, 97%) which was triturated with ether (10 ml). The solid was collected and dried in vacuo at 25° C. to give the alcohol as a colorless solid (27 mg), m.p. 136°–138° C., [α]$_d$ –38.3° (c=0.094, MeOH).

Elementary analysis for C$_{27}$H$_{31}$N$_3$O$_4$S.H$_2$O: Calculated; C 63.38; H 6.50; N 8.21%. Found; C 63.21; H 6.38; N 7.83%.

EXAMPLE 55

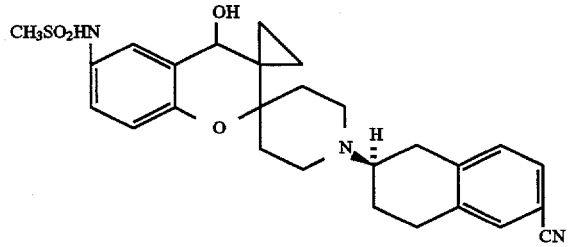

(+)-(4'RS,2'''R)-1''-[(6-Cyano-1,2,3,4-tetrahydronaphthalene)-2-yl]-6'-methanesulfonamidodispiro[cyclopropane-1,3'(4'H)-[2H-1]benzopyran-2',4''-piperidine]-4'-ol Lithium borohydride (34 mg, 1.56 mmol) was added to a stirred suspension of (+)-(2'''R)-1''-[(6-cyano-1,2,3,4- tetrahydronaphthalene)-2-yl]-6'-methanesulfonamidodispiro[cyclopropane-1,3'(4'H)-[2H-1]benzopyran-2',4"-piperidine]-4'-one (192 mg, 0.39 mmol) in THF (10 ml) and the yellow solution was stirred at room temperature for 17 h. Methanol (1 ml) was added and the mixture was poured into saturated aqueous sodium hydrogen carbonate (40 ml) and water (10 ml). The mixture was extracted with methylene chloride (3×40 ml) and the combined organic fractions were dried ($Na_2SO_4$) and evaporated under reduced pressure. Methanol (50 ml) was added and the volume was reduced by distillation to 25 ml. Further methanol (25 ml) was added and the volume was reduced by distillation to 25 ml. The solvent was evaporated under reduced pressure and the residue was purified by flash column chromatography on silica gel, eluting with $CH_2Cl_2$/$MeOH$/$NH_3$ (Aq.) (96:4:0.4 increasing to 90:10:1) to give a colorless foam (172 mg, 89%) which was triturated with ether (10 ml). The solid was collected and dried in vacuo at 25° C. to give the alcohol as a colorless solid (99 mg), m.p. 136°–138° C., $[\alpha]_d$ +37.7° (c=0.104, MeOH).

Elementary analysis for $C_{27}H_{31}N_3O_4S \cdot 0.5H_2O$: Calculated; C 64.51; H 6.42; N 8.36%. Found; C 64.69; H 6.55; N 8.03%.

EXAMPLE 56

IN VITRO TEST FOR CLASS III ANTIARRHYTHMIC ACTIVITY

PURPOSE:

This in vitro assay is designed to assess possible potassium channel blocking activity of a compound based on its ability to prolong effective refractory period (ERP) in isolated papillary muscle.

TISSUE PREPARATION:

Ferrets (700 to 1200 grams) are anesthetized with 0.7 ml of a mixture of xylazine and ketamine HCL in 1:7 ratio. Papillary muscles from the right ventricle are quickly excised from the isolated heart and mounted in 50 ml organ baths containing Krebs-Henseleit solution (pH=7.2–7.4) at 37 degrees Centigrade. The composition of the solution in millimoles per liter are as follows: NaCl, 118; KCl, 4.7; $NaCO_3$, 23; $CaCl_2 2H_2O$, 2; $MGSO_4$, $7H_2O$, 1.2; $KH_2PO_4$, 1.2; Dextrose, 11.1. Timolol (10–7M) is added to the solution to block the effects of released during stimulation of the muscles. This solution is aerated with 95% $O_2$ and 5% $CO_2$. The tissue is stimulated at 1 Hz at one msec pulse duration by a square wave stimulator at a voltage 30% above the threshold through platinum electrodes that touch the tissue just above the bottom attachment point. The tendenous end of the tissue is connected by thread to an isometric force transducer leading to a polygraph.

EFFECTIVE REFRACTORY PERIOD (ERP) MEASUREMENT

The ERP is determined by a standard 2 pulse protocol. Both pulses are stimulated at 1.3×voltage threshold. While pacing the tissue at a basal frequency of 1 Hz, a single extrastimulus is delivered after a variable time delay. The shortest delay resulting in a propagated response is defined as the ERP.

PROTOCOL:

1. Tissues are mounted with a resting tension of 0.5 gms, stimulated at 1 Hz, and allowed to equilibrate for 2 hours with washings at 15–20 minute intervals.

2. Voltage is adjusted to 30% above threshold and resting tension is adjusted for maximum developed reequilibration time.

3. Effective refractory period is measured at 1 Hz. Changes in resting tension and developed force are noted.

4. After equilibration, ERP's and developed force are measured at 30 minutes following the addition of increasing cumulative concentrations for test agent to the organ bath. Four to five concentrations of test agents were used to generate a concentration-response curve.

5. Four tissues per compound are tested.

RESULTS:

Employing the above protocol, it has been found that the effective concentration of most of the compounds of this invention required to increase the refractory period by an increment of 25% above base-line is less than or equal to 10 micro molar, i.e. $EC_{25}$ less than or equal to 10 micromolar, whereas sotalol in the same protocol has an $EC_{25}$ of approximately 20 micromolar.

EXAMPLE 57

PREPARATION OF INTRAVENOUS SOLUTIONS

A solution containing 0.5 mg of active ingredient per ml of indictable solution is prepared in the following manner.

A mixture of 0.5 mg of active ingredient is dissolved in 1 ml of acetate buffer. The pH is adjusted using hydrochloric acid or aqueous sodium hydroxide to about pH 5.5.

If it is desired that the intravenous solution be used for multi-dose purposes, 1.0 mg of methyl-p-hydroxy benzoate (methyl paraben) and 0.10 mg of n-propyl-p-hydroxy benzoate (propyl paraben) are mixed with the other solids before adding water to dissolve the solids. The solution is prepared and stored in such a manner that it is suitably protected from the deleterious effects of the atmosphere. One method by which this can be accomplished is by preparation and storage of the solution in an atmosphere of nitrogen. The resulting solution is sterilized by autoclaving. Injectable solutions comprising 0.001, 0.01 and 0.1 mg, respectively, of active ingredient per ml of solution are similarly prepared substituting the indicated amount for the above-illustrated 10 mg quantity. Bulk injectable solutions of convenient volume for subsequent delivery in unit dosage form are readily prepared following the above procedure.

EXAMPLE 58

TABLET PREPARATION

Tablets containing 1.0, 2.0, 25, 26.0, 50.0 and 100.0 mg, respectively, of active ingredient are prepared as illustrated below.

| TABLE FOR DOSES CONTAINING FROM 1–25 MG OF THE ACTIVE COMPOUND | | | |
|---|---|---|---|
| | Amount in mg | | |
| Active ingredient | 1.0 | 2.0 | 25.0 |
| Microcrystalline cellulose | 49.25 | 48.75 | 37.25 |

-continued

TABLE FOR DOSES CONTAINING FROM 1–25 MG OF THE ACTIVE COMPOUND

| | Amount in mg | | |
|---|---|---|---|
| Modified food corn starch | 49.25 | 48.75 | 37.25 |
| Magnesium stearate | 0.50 | 0.50 | 0.50 |

TABLE FOR DOSES CONTAINING FROM 26–100 MG OF THE ACTIVE COMPOUND

| | Amount in mg | | |
|---|---|---|---|
| Active ingredient | 26.0 | 50.0 | 100.0 |
| Microcrystalline cellulose | 25.0 | 100.0 | 200.0 |
| Modified food corn starch | 0.39 | 4.25 | 8.5 |
| Magnesium stearate | 0.39 | 0.75 | 1.50 |

All of the active compound, cellulose, and a portion of the corn starch are mixed and granulated to a 10% corn starch paste. The resulting granulation is sieved, dried and blended with the remainder of the corn starch and the magnesium stearate. The resulting granulation is then compressed into tablets containing 1.0 mg, 2.0 mg, 25.0 mg, 26.0 mg, 50 mg, and 100 mg of active ingredient per tablet.

While the foregoing specification teaches the principles of the present invention, with examples provided for the purpose of illustration, it will be understood that the practice of the invention encompasses all of the casual variations, adaptations, modifications, deletions, or additions of procedures and protocols described herein, as come within the scope of the following claims and its equivalents.

What is claimed is:

1. A compound of the structural formula:

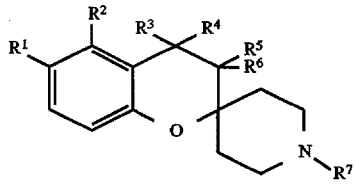

or a pharmaceutically acceptable salt, hydrate or crystal form thereof; wherein:

$R^1$=CH$_3$SO$_2$NH—, CH$_3$O—, alkylSO$_2$—, alkylCONH—, NO$_2$—;

$R^2$=H, —OCH$_3$;

$R^3$=—H, —OH;

$R^4$=H, OH; or $R^3$ and $R^4$ taken together are =O;

$R^5$=$R^6$ taken together are —CH$_2$—CH$_2$—, =CH$_2$; and $R^7$=

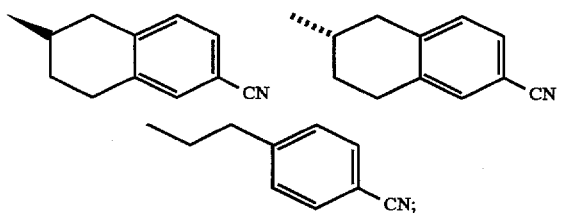

or the hydrochloride, maleate, methanesulfonate, tri-citrate or isothionate salt of these compounds.

2. The compound of claim 1, or a pharmaceutically acceptable salt, hydrate or crystal form thereof, wherein, $R^1$=CH$_3$SO$_2$NH—;

$R^2$=H;

$R^3$=—H, —OH;

$R^4$=—H, —OH, or $R^3$ and $R^4$ taken together as =O;

$R^5$ and $R^6$ taken together are =CH$_2$, —CH$_2$—CH$_2$—;

$R^7$=

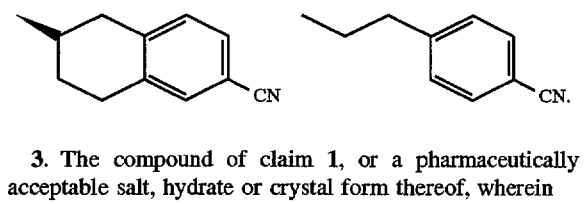

3. The compound of claim 1, or a pharmaceutically acceptable salt, hydrate or crystal form thereof, wherein $R^1$=CH$_3$SO$_2$NH—;

$R^2$=—H;

$R^3$=—OH;

$R^4$=—H;

$R^5$ and $R^6$ taken together are =CH$_2$, —CH$_2$—CH$_2$—;

$R^7$=

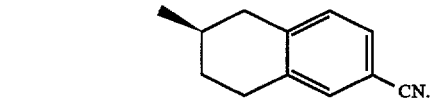

4. The compound of claim 1, or a pharmaceutically acceptable salt, hydrate or crystal form thereof, wherein $R^1$=CH$_3$SO$_2$NH—;

$R^2$=—H;

$R^3$ and $R^4$ taken together are =O;

$R^5$ and $R^6$ taken together are =CH$_2$, —CH$_2$—CH$_2$—;

$R^7$ is

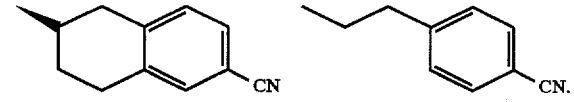

5. The compound of claim 1 or a pharmaceutically acceptable salt, hydrate or crystal form thereof, where $R^1$=CH$_3$SO$_2$NH—;

$R^2$=—H;

$R^3$=—H;

$R^4$=—OH;

$R^5$ and $R^6$ taken together are —CH$_2$—CH$_2$—;

$R^7$ is

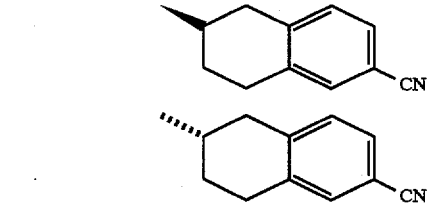

6. The compound of claim 1 or a pharmaceutically acceptable salt hydrate or crystal form thereof, wherein
$R^1$=CH$_3$SO$_2$NH—;
$R^2$=—H;
$R^3$ and $R^4$ taken together are =O;
$R^5$ and $R^6$ taken together are —CH$_2$—CH$_2$—;
$R^7$ is or the hydrochloride, maleate, methanesulfonate, tri-citrate or isethionate salt of this base.

7. The compound of claim 1 or a pharmaceutically acceptable salt, hydrate or crystal form thereof, wherein
$R^1$=CH$_3$SO$_2$NH—;
$R^2$=—H;
$R^3$ and $R^4$ taken together are =O;
$R^5$ and $R^6$ taken together are —CH$_2$—CH$_2$—;
$R^7$ is or the hydrochloride, maleate, methanesulfonate, tri-citrate or isethionate salt of this base.

8. The compound of claim 1 or a pharmaceutically acceptable salt, hydrate, or crystal form thereof, wherein
$R^1$=CH3SO2NH—
$R^2$=—H;
$R^3$ and $R^4$ taken together are =O;
$R^5$ and $R^6$ taken together are —CH$_2$—CH$_2$—;
$R^7$ is

9. A compound selected from the group consisting of

1'-[2-(4-Cyanophenyl)ethyl]-3,4-dihydro-6-methanesulfonamido-3-methylenespiro(2H-1-benzopyran-2,4'-piperidine)-4-one 1"-[2-(4-Cyanophenyl)ethyl]-6'-methanesulfonamidodispiro[cyclopropane-1,3'(4'H)-[2H-1]benzopyran-2',4"-piperidine]-4'-one 1"-[2-(4-Cyanophenyl)ethyl]-6'-methanesulfonamidodispiro[cyclopropane-1,3'(4'H)-[2H-1]benzopyran-2',4"-piperidine]-4'-one hydrochloride 1"-[2-(4-Cyanophenyl)ethyl]-6'-methanesulfonamidodispiro[cyclopropane-1,3'(4'H)-[2H-1]benzopyran-2',4"-piperidine]-4'-one maleate 1"-[2-(4-Cyanophenyl)ethyl]-6'-methanesulfonamidodispiro[cyclopropane-1,3'(4'H)-[2H-1]benzopyran-2',4"-piperidine]-4'-one methanesulfonate

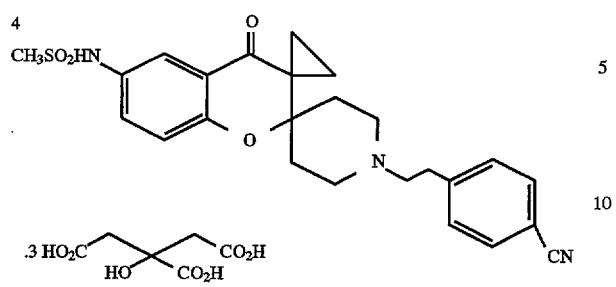

Tetra{1"-[2-(4-cyanophenyl)ethyl]-6'-methanesulfonamidodispiro[cyclopropane-1,3'(4'H)-[2H-1]benzopyran-2',4"-piperidine]-4'-one}tricitrate

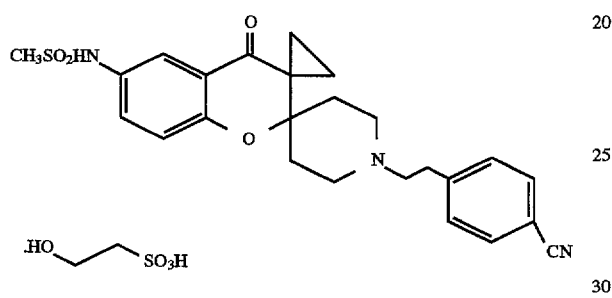

1"-[2-(4-Cyanophenyl)ethyl]-6'-methanesulfonamidodispiro[cyclopropane-1,3'(4'H)-[2H-1]benzopyran-2',4"-piperidine]-4'-one isethionate

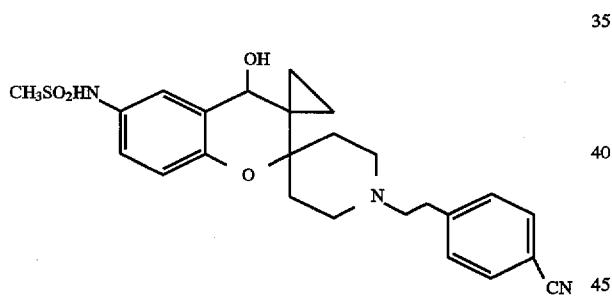

(4'RS)-1"-[2-(4-Cyanophenyl)ethyl]-6'-methanesulfonamidodispiro[cyclopropane-1,3'(4'H)-[2H-1]benzopyran-2',4"-piperidine]-4'-ol

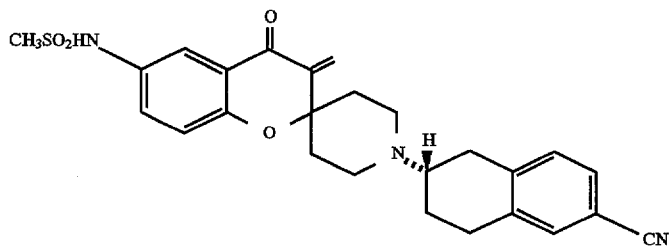

(−)-(2"S)-1'-[(6-Cyano-1,2,3,4-tetrahydronaphthalene)-2-yl]-3,4-dihydro-6-methanesulfonamido-3-methylenespiro(2H-1-benzopyran-2,4'-piperidine)-4-one

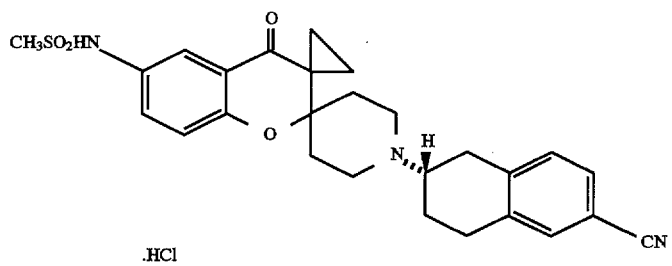

(−)-(2′″S)-1″-[(6-Cyano-1,2,3,4-tetrahydronaphthalene)-2-yl]-6′-methanesulfonamidodispiro[cyclopropane-1,3′ (4′H)-[2H-1]benzopyran-2′,4″-piperidine]-4′-one hydrochloride

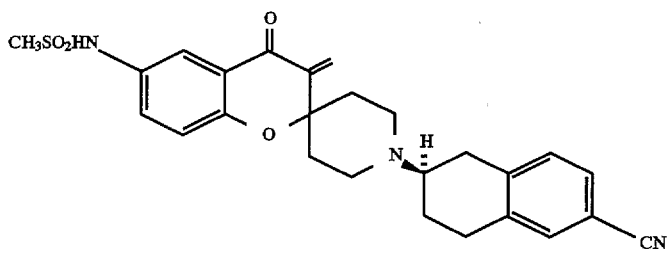

(+)-(2″R)-1′-[(6-Cyano-1,2,3,4-tetrahydronaphthalene)-2-yl]-3,4-dihydro-6-methanesulfonamido-3-methylenespiro(2H-1-benzopyran-2,4′-piperidine)-4-one

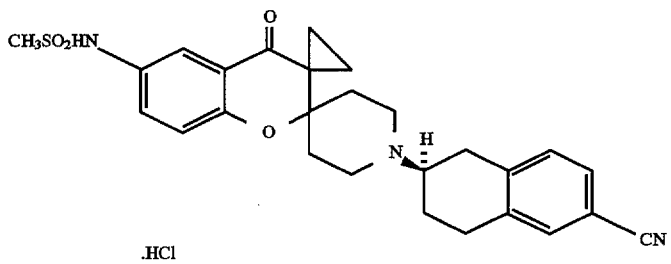

(+)-(2′″R)-1″-[(6-Cyano-1,2,3,4-tetrahydronaphthalene)-2-yl]-6′-methanesulfonamidodispiro[cyclopropane-1,3′ (4′H)-[2H-1]benzopyran-2′,4″-piperidine]-4′-one hydrochloride

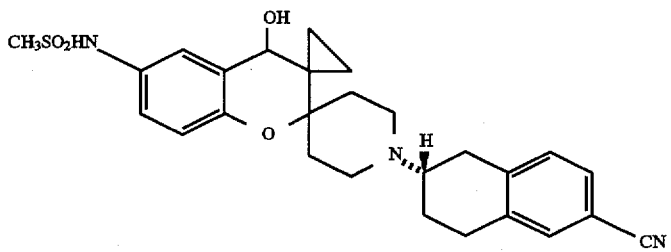

(−)-(4′RS,2′″S)-1″-[(6-Cyano-1,2,3,4-tetrahydronaphthalene)-2-yl]-6′-methanesulfonamidodispiro[cyclopropane-1,3′(4′H)-[2H-1]benzopyran-2′,4″-piperidine]-4′-ol; or

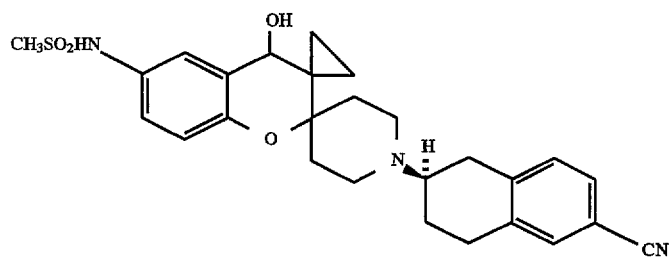

(+)-(4'RS,2'"R)-1"-[(6-Cyano-1,2,3,4-tetrahydronaphthalene)-2-yl]-6'-methanesulfonamidodispiro[cyclopropane-1,3'(4'H)-[2H-1]benzopyran-2',4"-piperidine]-4'-ol.

10. A pharmaceutical formulation comprising a carrier and a therapeutically effective amount of a compound of claim 1.

11. A method of treating arrhythmia and/or impaired cardiac pump function in a patient in need of such treatment which comprises administering to such patient a therapeutically effective amount of the compound of claim 1.

* * * * *